US008357369B2

(12) United States Patent
Lenz

(10) Patent No.: US 8,357,369 B2
(45) Date of Patent: Jan. 22, 2013

(54) GENETIC MARKERS FOR PREDICTING RESPONSIVENESS TO COMBINATION THERAPY

(75) Inventor: Heinz-Josef Lenz, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/249,148

(22) Filed: Sep. 29, 2011

(65) Prior Publication Data

US 2012/0020984 A1    Jan. 26, 2012

Related U.S. Application Data

(63) Continuation of application No. 12/523,522, filed as application No. PCT/US2008/000650 on Jan. 17, 2008, now abandoned.

(60) Provisional application No. 60/885,608, filed on Jan. 18, 2007, provisional application No. 60/881,240, filed on Jan. 18, 2007, provisional application No. 60/915,576, filed on May 2, 2007.

(51) Int. Cl.
*A61K 39/395* (2006.01)
(52) U.S. Cl. ............... 424/141.1; 435/6.14; 435/7.23
(58) Field of Classification Search .............. None
See application file for complete search history.

(56) References Cited

U.S. PATENT DOCUMENTS

2005/0064417 A1* 3/2005 Watier et al. ........... 435/6

FOREIGN PATENT DOCUMENTS

| WO | WO 03/035904 A2 | 5/2003 |
| WO | WO 2004/063351 A2 | 7/2004 |
| WO | WO 2005/012358 A2 | 2/2005 |
| WO | WO 2005/062929 A2 | 7/2005 |
| WO | WO 2005/102379 A1 | 12/2005 |
| WO | WO 2005/118854 A1 | 12/2005 |
| WO | WO 2007/064957 A1 | 6/2007 |
| WO | WO 2008/088860 A2 | 7/2008 |

OTHER PUBLICATIONS

CALGB/SWOG, Clin Adv Hemat Oncol, 2006, 6:452-453.*
Adams, Am J Health Syst Pharm, 2006, s4-11.*
Hatjiharissi et al, Blood, 2007, 110:2561-2564.*
Dall'Ozzo et al Cancer Res, 2004, 64:4664-4669.*
Yan et al, Pharmacogenomics, 2006, 7:961-964.*
Zhang et al, J Clin Oncol, 2007, 25:3712-3718.*
Bibeau et al, J Clin Oncol, 2009, 27:1122-1129.*
Cartron et al. (2002) "Therapeutic activity of humanized anti-CD20 monoclonal antibody and polymorphism in IgG Fc receptor FcγRIIIa gene," Blood 99:754-8, 2002.
Cunningham et al. (2004) "Cetuximab Monotherapy and Cetuximab Plus Irinotecan in Irinotecan-Refractory Metastatic Colorectal Cancer," New England Journal of Medicine 351( 4):337-345.
Dalhoff et al. (2005) "Cancer and Molecular Biomarkers of Phase 2," Methods in Enzymology 400:618-627.
Dunning et al. (2003) "A Transforming Growth Factor Beta1 Signal Peptide Variant Increases Secretion in Vitro and Is Associated with Increased Incidence of Invasive Breast Cancer," Cancer Research 63(10):2610-2615.
Graziano et al. (2008) "Pharmacogenetic profiling for cetuximab plus irinotecan therapy in patients with refractory advanced colorectal cancer," Journal of Clinical Oncology 26(9):1427-1434.
Gruel et al. (2004) "The homozygous FcγRIIIa-158V genotype is a risk factor for heparin-induced thrombocytopenia in patients with antibodies to heparin-platelet factor 4 complexes," Blood 104(9):2791-2793.
Hatjiharissi et al. (2005) "Individuals Expressing FC Gamma RIIIa-158 V/V and V/F Show Increased NK Cell Surface Expression of FcgRIIIA (CD16), Rituximab Binding, and Demonstrate Higher Levels of ADCC Activity in Response to Rituximab," Blood 106(11) Part 1: 229A.
Hinoda et al. (2004) "Monoclonal Antibodies as Effective Therapeutic Agents for Solid Tumors," Cancer Science 95( 8):621-625.
International Search Report for PCT Application No. PCT/US2008/000650, dated Jun. 19, 2008.
Lehrnbecher et al. (1999) "Variant Genotypes of the Low-Affinity Fcγ Receptors in Two Control Populations and a Review of Low-Affinity Fcγ Receptor Polymorphisms in Control and Disease Populations," Blood 94:4220-4232.
Lurje et al. (2008) "Polymorphisms in *Cyclooxygenase-2* and *Epidermal Growth Factor Receptor* are Associated with Progression-Free Survival Independent of K-ras in Metastatic Colorectal Cancer Patients Treated with Single-Agent Cetuximab," Clin. Cancer Res. 14(23):7884-7895.
Paez et al. (2010) "Immunoglobulin G fragment C receptor polymorphisms and KRAS mutations: Are they useful biomarkers of clinical outcome in advanced colorectal cancer treated with anti-EGFR-based therapy?" Cancer Science, 101(9):2048-2053.
Pander et al. (2007) "Pharmacogenetics of EGFR and VEGF Inhibition," Drug Disc Today 12( 23-24):1054-1060.
Peterson et al. (2005) "*Cruciferae* Interact with the UGT1A1*28 Polymorphism to Determine Serum Bilirubin Levels in Humans," The Journal of Nutrition 135( 5):1051-1055.

(Continued)

*Primary Examiner* — Misook Yu
*Assistant Examiner* — Mark Halvorson
(74) *Attorney, Agent, or Firm* — Foley & Lardner LLP; Antoinette F. Konski; Alex Y. Nie

(57) ABSTRACT

The invention provides compositions and methods for determining the likelihood of successful treatment with an effective amount of an anti-VEGF antibody or equivalent thereof, in combination with anti-EGFR antibody or equivalent thereof, and, in some aspects in combination with a topoisomerase inhibitor. The methods comprise determining the identity of a gene of interest in a patient sample and correlating the patient's genotype with the predictive response. Patients identified as responsive are then treated with the appropriate therapy.

14 Claims, 12 Drawing Sheets

OTHER PUBLICATIONS

Stoehlmacher et al. (2004) "A Multivariate Analysis of Genomic Polymorphisms: Prediction of Clinical Outcome to 5-FU/oxaliplatin Combination Chemotherapy in Refractory Colorectal Cancer," British Journal of Cancer 91(2):344-354.

Stoehlmacher (2005) "Pharmacogenetics in Gastrointestinal Tumors," Onkologie 28(8-9):435-440.

Vallbohmer et al. (2005) "Molecular Determinants of Cetuximab Efficacy," Journal of Clinical Oncology: Official Journal of the American Society of Clinical Oncology 23(15):3536-3544.

Weng et al. (2003) "Two Immunoglobulin G Fragment C Receptor Polymorphisms Independently Predict Response to Rituximab in Patients with Follicular Lymphoma," J Clin Oncol 21:3940-3947.

Wiedmann et al. (2005) "Moleculary Targeted Therapy for Gastrointestinal Cancer," Current Cancer Drug Targets 5:171-193.

Yan et al. (2005) "Pharmacogenetics and Pharmacogenomics in Oncology Therapeutic Antibody Development," Biotechniques 39(4):565-568.

Zhang et al. (2005) "Cyclin D1 and Epidermal Growth Factor Polymorphisms Associated with Survival in Patients with Advanced Colorectal Cancer Treated with Cetuximab," Pharmacogenetics and Genomics 16(7):475-83.

* cited by examiner

```
                        SEQUENCE LISTING

<160> NUMBER OF SEQ ID NOS: 59

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagcgcggct acagctt                                                      17

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tccttaatgt cacgcacgat tt                                                22

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
accaccacgg ccgagcgg                                                     18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctgtggctc tgcgtgga                                                     18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgagcctgg gcagatcaag                                                   20

<210> SEQ ID NO 6
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cactaggcaa acccacagag gcggc                                             25

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccgcctgaac taccctgag                                                    19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcagaaggcc caagtctacc                                                   20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcccggagag gattcctacc ga                                                22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggaatttgg cgacgtaatt c                                                 21

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcggaggctg aggaacag                                                     18

<210> SEQ ID NO 12
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 12
cacaggtgct ctggcccagc acata                                           25

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agtggtccca ggctgcac                                                   18

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tccatgaact tcaccacttc gt                                              22

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atggcagaag gaggagggca gaatca                                          26

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgcgtctctt gccggaat                                                   18

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggctcaccct ccagaagctt                                                 20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued

```
                                    primer

<400> SEQUENCE: 18
acgcattccc tgcctcggct g                                              21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctcaacatg atgtttgcat tc                                             22

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gctggccctc gcttatga                                                  18

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgcccagcac ttcacgcatc agtt                                           24

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgcatgttcg tggcctctaa                                                20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcggtgtaga tgcacagctt ct                                             22

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 24
aaggagacca tccccctgac ggc                                              23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cagctctgtg tgaaggtgca gtt                                              23

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggtggaaag gtttggagta tgtc                                             24

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgcactgaca tctaagttct ttagcactcc ttggc                                 35

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgccgccctc cgggctgcgg ctgcggc                                          27

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tcttgcaggt ggatagtccc gcggtcgg                                         28

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
ctgaagacac atttttactc ccaam                                          25
```

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
tccaaaagcc acactcaaag ac                                             22
```

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
cctctcccctt tcctctgttc                                               20
```

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
caggtgaggg ggacatct                                                  18
```

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
cccaatggat gatgacttcc                                                20
```

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

```
agtggtggca ttagcagtag g                                              21
```

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
gcaaaatgtt taattcagtg atgttc                                         26
```

```
<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcccactatc tcaggtgatg c                                           21

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctaagaggag cccttcccta tgt                                         23

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aatacgggcc tagatctgaa tgtg                                        24

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtgaagttca tttccaatcc gc                                          22

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggacatcacc ctcacttac                                              19

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtcacgtgac acagtcaaac                                             20

<210> SEQ ID NO 43
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tttgctcctg ccagaggtt                                                19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgctgtgacc cactctgtct                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccagaaggtt gcacttgtcc                                               20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcagagctca cctgaggaac                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gaggtgcaag aagaggtgga                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
accccagggc tctatgggaa                                               20

<210> SEQ ID NO 49
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 49
tgagggcaca agaagcccct                                              20

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aaggaagagg agactctgcg cagagc                                       26

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
taaatgtatg tatgtgggtg ggtgtgtcta cagg                              34

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttgttctaac acctgccact ct                                           22

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggcaaacctg agtctcaca                                               19

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccgcttcctt tgtccatcag                                              20

<210> SEQ ID NO 55
<211> LENGTH: 23
<212> TYPE: DNA
<213> ORGANISM: Artificial Sequence
<220> FEATURE:

-continued

```
<223> OTHER INFORMATION: Description of Artificial Sequence: Synthetic
      primer

<400> SEQUENCE: 55
ggctgtatat ctgctctata tgc                                             23

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcccaggtct tagtgagcca                                                 20

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acgactaacc gacaccgg                                                   18

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
taaggagtgg gtgccggact gtc                                             23

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
agtagtctgc tggctctgg                                                  19
```

GENETIC MARKERS FOR PREDICTING RESPONSIVENESS TO COMBINATION THERAPY

CROSS-REFERENCE TO RELATED APPLICATIONS

This application claims the benefit under 35 U.S.C. §119(e) of provisional applications U.S. Ser. Nos. 60/885,608 filed on Jan. 18, 2007; 60/881,240 filed on Jan. 18, 2007 and 60/915,576, filed on May 2, 2007. The contents of each of these applications are incorporated by reference into the present disclosure in their entirety.

FIELD OF THE INVENTION

This invention relates to the field of pharmacogenomics and specifically to the application of genetic polymorphism(s) to diagnose and treat diseases.

BACKGROUND OF THE INVENTION

In nature, organisms of the same species usually differ from each other in some aspects, e.g., their appearance. The differences are genetically determined and are referred to as polymorphism. Genetic polymorphism is the occurrence in a population of two or more genetically determined alternative phenotypes due to different alleles. Polymorphism can be observed at the level of the whole individual (phenotype), in variant forms of proteins and blood group substances (biochemical polymorphism), morphological features of chromosomes (chromosomal polymorphism) or at the level of DNA in differences of nucleotides (DNA polymorphism).

Polymorphism also plays a role in determining differences in an individual's response to drugs. Pharmacogenetics and pharmacogenomics are multidisciplinary research efforts to study the relationship between genotype, gene expression profiles, and phenotype, as expressed in variability between individuals in response to or toxicity from drugs. Indeed, it is now known that cancer chemotherapy is limited by the predisposition of specific populations to drug toxicity or poor drug response. For a review of the use of germline polymorphisms in clinical oncology, see Lenz (2004) J. Clin. Oncol. 22(13):2519-2521; Park et al. (2006) Curr. Opin. Pharma. 6(4):337-344; Zhang et al. (2006) Pharma. and Genomics 16(7):475-483 and U.S. Patent Publ. No. 2006/0115827. For a review of pharmacogenetics and pharmacogenomics in therapeutic antibody development for the treatment of cancer, see Yan and Beckman (2005) Biotechniques 39:565-568 and Lenz, H.-J., Pharmacogenomics and Colorectal Cancer, Chpt. 18 in TRENDS IN CANCER FOR THE 21$^{ST}$ CENTURY, 2$^{nd}$ Ed., Springer (2006).

Colorectal cancer (CRC) represents the second leading lethal malignancy in the USA. In 2005, an estimated 145,290 new cases will be diagnosed and 56,290 deaths will occur. Jemal et al. (2005) Cancer J. Clin. 55:10-30. Despite advances in the treatment of colorectal cancer, the five year survival rate for metastatic colon cancer is still low, with a median survival of 18-21 months. Douglass et al. (1986) N. Eng. J. Med. 315:1294-1295.

The Food and Drug Administration has approved the use of Cetuximab, an antibody to the epidermal growth factor receptor (EGFR), either alone or in combination with irinotecan (also known as CPT-11 or Camptosar®) to treat patients with EGFR-expressing, metastatic CRC, who are either refractory or intolerant to irinotecan-based chemotherapy. One recent study (Zhang et al. (2006) Pharmacogenetics and Genomics 16:475-483) investigated whether polymorphisms in genes of the EGFR signaling pathway are associated with clinical outcome in CRC patients treated with single-agent Cetuximab. The study reported that the Cyclin D1 (CCND1) A870G and the EGF A61G polymorphisms may be useful molecular markers for predicting clinical outcome in CRC patients treated with Cetuximab.

Other polymorphisms have been reported to be associated with clinical outcome. Twenty-one (21) polymorphisms in 18 genes involved in the critical pathways of cancer progression (i.e., drug metabolism, tumor microenvironment, cell cycle regulation, and DNA repair) were investigated to determine if they will predict the risk of tumor recurrence in rectal cancer patients treated with chemoradiation. Gordon et al. (2006) Pharmacogenomics 7(1):67-88.

In addition to genetic polymorphisms being predictive molecular markers, gene expression levels have also been examined for their association with cancer patient clinical outcome. One study (Vallbohmer et al. (2005) J. Clin. Oncol. 23(15):3536-3544) showed that gene expression levels of COX-2, EGFR, IL-8, and VEGF in patients with metastatic CRC may be useful markers of clinical outcome in single-agent Cetuximab treatment. Additionally, gene expression of VEGF, survivin, and EGFR could be associated with lymph node involvement in patients with locally advanced rectal cancer describe in Yang et al (2006) Clin. Colorectal Cancer 6(4):305-311. However, to the best of Applicant's knowledge, correlation of the genetic markers identified herein and responsiveness to combination therapy has not been previously reported.

DESCRIPTION OF THE EMBODIMENTS

This invention provides methods to identify patients likely responsive to a selected therapy and to select the appropriate therapy for patients suffering from a gastrointestinal cancer, wherein the appropriate therapy comprises administration of an effective amount of an anti-VEGF antibody or equivalent thereof, in combination with anti-EGFR antibody or equivalent thereof, and, in some aspects in combination with a topoisomerase inhibitor.

This invention also provides methods to identify patients likely responsive to a selected therapy and to select the appropriate therapy for patients suffering from a gastrointestinal cancer, wherein the appropriate therapy comprises administration of an effective amount of Bevacizumab (BZ) (a/k/a Avastin®) in combination with Cetuximab (a/k/a Erbitux®) and, in some aspects in combination with Irinotecan (a/k/a Camptosar®). The method requires detecting the identity of at least one genetic marker from the group identified in Tables 1, 2, or 4 below.

TABLE 1

Combination Anti-VEGF, Anti-EGFR and Topoisomerase Inhibitor

| Allele | Predictive Polymorphism Genotype | Measured Response |
|---|---|---|
| TGF-β (T29C) | C/C or T/T | Reduction in Tumor Load or Size |
| CCND1 (A870G) | A/A or G/G | Increase or Elongation or Time to Tumor Progression |
| UGT1A1 (UGT1A1*28) | 6/6, 6/7, or 8 | Increase or Elongation of Time to Tumor Progression |

TABLE 1-continued

Combination Anti-VEGF, Anti-EGFR and Topoisomerase Inhibitor

| Allele | Predictive Polymorphism Genotype | Measured Response |
|---|---|---|
| EGFR (G497A) | G/G or G/A | Increase or Elongation of Overall Survival |
| ERCC1 (C118T) | C/C or T/T | Increase or Elongation of Time to Tumor Progression |
| GSTP1 (V105I) | V/I or I/I | Increase or Elongation of Overall Survival |

TABLE 2

Combination Anti-VEGF and Anti-EGFR Therapy

| Allele | Predictive Polymorphism Genotype | Measured Response |
|---|---|---|
| FCGRIIIA (V158F) | F/F or V/F | Reduction in Tumor Load or Size |
| XPD (A751C) | A/A or A/C | Increase or Elongation of Time to Tumor Progression and Overall Survival |
| TGF-β (T29C) | C/C or T/T | Reduction in Tumor Load or Size and Increase or Elongation of Time to Tumor Progression |
| HIF1α (C1772T) | C/T or T/T | Reduction in Tumor Load or Size |
| FCGRIIB (T232C) | T/T or T/c | Increase or Elongation of Time to Tumor Progression |
| OATPC (A388G) | A/A | Increase or Elongation of Overall Survival |

TABLE 3

Additional Polymorphisms Assayed - No Correlation

| Allele | Measured Response |
|---|---|
| VEGF (+936C/T) | No Correlation |
| IL-8 (−251T/A) | No Correlation |
| COX-2 (−765G/C) | No Correlation |
| E-cadherin (−160C/A) | No Correlation |
| XRCC1 (R399Q) | No Correlation |

TABLE 4

Combination Anti-VEGF, Anti-EGFR and Topoisomerase Inhibitor

| Allele | Gene Expression Ratio To Internal Control | Measured Response |
|---|---|---|
| VEGFR2 | High expression | Responder |
| NRP1 | Low expression | |
| VEGFR2 | High expression | Non-Responder |
| NRP1 | High expression | |
| VEGFR2 | Low expression | Non-Responder |
| NRP1 | High expression | Time to Tumor |

TABLE 4-continued

Combination Anti-VEGF, Anti-EGFR and Topoisomerase Inhibitor

| Allele | Gene Expression Ratio To Internal Control | Measured Response |
|---|---|---|
| ERCC1 | Low expression | Progression (Low Risk) |
| NRP1 | High expression | Time to Tumor |
| ERCC1 | High expression | Progression (Intermediate Risk) |
| NRP1 | Low expression | Time to Tumor Progression (High Risk) |
| EGFR | High expression | Overall Survival (Low Risk) |
| EGFR | Low expression | Overall Survival |
| VEGFR2 | High expression | (Intermediate Risk) |
| EGFR | Low expression | Overall Survival |
| VEGFR2 | Low expression | (High Risk) |
| VEGFA | Cut-off value selected by CART analysis | No Correlation |
| COX2 | Cut-off value selected by CART analysis | No Correlation |
| Cyclin D1 | Cut-off value selected by CART analysis | No Correlation |
| IL-8 | Cut-off value selected by CART analysis | No Correlation |

This invention also provides methods for treating gastrointestinal cancer or malignant tumors by administering an effective amount of an anti-VEGF antibody or equivalent thereof, in combination with anti-EGFR antibody or equivalent thereof, and, in some aspects in combination with a topoisomerase inhibitor. In another aspect, the therapy comprises administration of an effective amount of BZ alone or in combination with Cetuximab (C) and/or further with Irinotecan (I), or an equivalent of each of these biological or chemical therapies.

The various embodiments are set forth herein.

In one aspect, the invention is a method for identifying responsiveness to combination Cetuximab, Bevacizumab, and Irinotecan (CBI) anti-tumor therapy, as examples of anti-VEGF antibody, anti-EGFR antibody, and topoisomerase I inhibitor therapy, by assaying a suitable patient sample from a patient suffering from a solid malignant tumor or metastatic or non-metastatic gastrointestinal cancer, for at least one genetic marker identified in the left hand column of Tables 1 and 4, above. Patients having a genetic marker selected from at least one, or alternatively at least two, or alternatively at least three, or alternatively at least four, or alternatively at least five, or alternatively at least six, or alternatively at least seven, or alternatively at least eight, or alternatively at least nine, or alternatively all ten of C/C or T/T (TGF-β T29C); A/A or G/G (CCND1 A870G); UGT1A1*28 for UGT1A1; G/G or G/A (EGFR G497A); high VEGFR2 expression and low NRP1 expression; high NRP1 expression and low ERCC1 expression; high EGFR expression; or low EGFR expression and high VEGFR2 expression, are likely to show responsiveness to CBI therapy, wherein responsiveness is any kind of improvement or positive response either clinical or non-clinical selected from, but not limited to, measurable reduction in tumor size or evidence of disease or disease progression, complete response, partial response, stable disease, increase or elongation of progression free survival, increase or elongation of overall survival, or reduction in toxicity. The correlation between the individual polymorphism or marker and its associated clinical outcome is provided in the right hand column of Tables 1, 2 and 4 and detailed in the experimental examples provided below.

In another aspect, alternative genetic markers can be used as negative controls with the methods identified above to screen for and identify a patient who is not likely to show responsiveness to CBI anti-tumor therapy, as identified in Tables 3 and 4 above. Patients having genetic markers selected from at least one, or alternatively at least two, or alternatively at least three, or alternatively at least four, or alternatively at least five, or alternatively at least six, or alternatively at least seven, or alternatively at least eight, or alternatively at least nine, or alternatively at least ten, or alternatively all eleven of VEGF (+936C/T); IL-8 (−251T/A); COX-2 (−765G/C); E-cadherin (−160C/A); ERCC1 (118C/T); XRCC1 (R399Q); GSTP1 (I105V); VEGFA high or low expression; COX2 high or low expression; Cyclin D1 high or low expression; or IL-8 high or low expression, will unlikely show responsiveness, wherein responsiveness is any kind of improvement or positive response either clinical or non-clinical selected from, but not limited to, measurable reduction in tumor size or evidence of disease or disease progression, complete response, partial response, stable disease, increase or elongation of progression free survival, increase or elongation of overall survival, or reduction in toxicity.

Suitable patients for the methods of this invention are those suffering from a metastatic or non-metastatic tumor such as a gastrointestinal tumor, e.g., from rectal cancer, colorectal cancer, colon cancer, gastric cancer, lung cancer, non-small cell lung cancer and esophageal cancer. In a further aspect, the patient has a tumor or neoplasm that is colorectal cancer. In a further aspect, the patient is suffering from metastatic colorectal cancer.

To practice this method, the sample is a patient sample containing the tumor tissue, normal tissue adjacent to said tumor, normal tissue distal to said tumor or peripheral blood lymphocytes. In a further aspect, the patient or patient population to be treated also is BZ naïve or an equivalent thereof.

In one aspect, the method also requires isolating a sample containing the genetic material to be tested; however, it is conceivable that one of skill in the art will be able to analyze and identify genetic markers in situ at some point in the future. Accordingly, the inventions of this application are not to be limited to requiring isolation of the genetic material prior to analysis.

These methods are not limited by the technique that is used to identify the polymorphism of interest. Suitable methods include but are not limited to the use of hybridization probes, antibodies, primers for PCR analysis, and gene chips, slides and software for high throughput analysis. Additional polymorphisms can be assayed and used as negative controls which include, but are not limited to those identified in Table 3, above.

These methods to identify gene expression levels are not limited by the technique that is used to identify the expression level of the gene of interest. Methods for measuring gene expression are well known in the art and include, but are not limited to, immunological assays, nuclease protection assays, northern blots, in situ hybridization, reverse transcriptase Polymerase Chain Reaction (RT-PCR), Real-Time Polymerase Chain Reaction, expressed sequence tag (EST) sequencing, cDNA microarray hybridization or gene chip analysis, subtractive cloning, Serial Analysis of Gene Expression (SAGE), Massively Parallel Signature Sequencing (MPSS), and Sequencing-By-Synthesis (SBS).

After a patient has been identified as likely to be responsive to the therapy based on the identity of one or more of the genetic markers identified in Tables 1 and 4, the method may further comprise administering or delivering an effective amount of a BZ antibody or biologically equivalent thereof and an effective amount of Cetuximab antibody or biologically equivalent thereof and an effective amount of Irinotecan or a chemical equivalent thereof, to the patient. Methods of administration of pharmaceuticals and biologicals are known in the art and are incorporated herein by reference.

In another aspect, the invention is a method for identifying responsiveness to combined Bevacizumab and Cetuximab (CB) therapy by assaying a suitable patient sample from a patient suffering from a solid malignant gastrointestinal tumor or gastrointestinal cancer, for at least one genetic marker identified in Table 2, above. Patients who are considered positive responders for further CB therapy have at least one, or alternatively at least two, or alternatively at least three, or alternatively at least four, or alternatively at least five, or alternatively all six genetic markers selected from F/F or V/F (FCGRIIIA V158F), A/A or A/C (XPD A751C), C/C or T/T (TGF-β T29C), C/T or T/T (HIF1-α C1772T), A/A (OATPC A388G), or T/T or T/C (FCGRIIB T232C). These patients are likely to show responsiveness to combined CB therapy or biologically equivalents thereof, wherein responsiveness is any kind of improvement or positive response either clinical or non-clinical selected from, but not limited to, measurable reduction in tumor size or evidence of disease or disease progression, complete response, partial response, stable disease, increase or elongation of progression free survival, increase or elongation of overall survival, or reduction in toxicity.

In another aspect, alternative genetic markers can be used as negative with the methods identified above to screen for and identify a patient who is not likely to show responsiveness to CB anti-tumor therapy, as identified in Table 4 above. Negative controls include at least one, or alternatively at least two, or alternatively at least three, or alternatively at least four, or alternatively at least five, or alternatively at least six, or alternatively all seven of VEGF (+936C/T); IL-8 (−251T/A); COX-2 (−765G/C); E-cadherin (−160C/A); ERCC1 C/T); XRCC1 (R399Q); or GSTP1 (I105V), will unlikely show responsiveness, wherein wherein responsiveness is any kind of improvement or positive response either clinical or non-clinical selected from, but not limited to, measurable reduction in tumor size or evidence of disease or disease progression, complete response, partial response, stable disease, increase or elongation of progression free survival, increase or elongation of overall survival, or reduction in toxicity.

In another aspect, the patient is suffering from a metastatic or non-metastatic tumor such as a gastrointestinal tumor, e.g., from rectal cancer, colorectal cancer, colon cancer, gastric cancer, lung cancer, non-small cell lung cancer and esophageal cancer. In a further aspect, the tumor or neoplasm is colorectal cancer.

To practice this method, the sample is a patient sample containing the tumor tissue, normal tissue adjacent to said tumor, normal tissue distal to said tumor or peripheral blood lymphocytes. In a further aspect, the patient or patient population to be treated also is BZ naïve.

In one aspect, the method also requires isolating a sample containing the genetic material to be tested; however, it is conceivable that one of skill in the art will be able to analyze and identify genetic markers in situ at some point in the future. Accordingly, the inventions of this application are not to be limited to requiring isolation of the genetic material prior to analysis.

These methods also are not limited by the technique that is used to identify the polymorphism of interest. Suitable methods include but are not limited to the use of hybridization probes, antibodies, primers for PCR analysis, and gene chips, slides and software for high throughput analysis. Additional genetic markers can be assayed and used as negative controls, which include, but are not limited to those identified in Table 3, above. Suitable negative controls are identified in the experimental section below.

After a patient has been identified as likely to be responsive to the therapy based on the based on the possession of at least one of the genetic markers identified in center column of Table 2, the method may further comprise administering or delivering an effective amount of a BZ antibody or biologically equivalent thereof and an effective amount of Cetuximab antibody or biologically equivalent thereof, to the patient. Methods of administration of pharmaceuticals and biologics are known in the art and are incorporated herein by reference.

In a further aspect, the invention is a method comprising comparing the genetic markers of a patient against the identified genetic markers of Tables 1, 2, 3 and 4 alone, in combination with Tables 1 and 2, in combination with Tables 1 and 3, in combination with Tables 1 and 4, in combination with Tables 2 and 3, in combinations with tables 2 and 4, in combination with Tables 3 and 4, in combination with Table 1, 2, and 3, in combination with Tables 1, 3 and 4, in combination with Tables 1, 2, and 4, in combination with Tables 2, 3, and 4, or in combination with Tables 1, 2, 3 and 4. Suitable patients for the method are those having a metastatic or non-metastatic gastrointestinal malignant tumor. If a patient has a genetic marker matching at least one, or alternatively at least two, or alternatively at least three, or at least four, or alternatively at least five, or alternatively all six of Table 1 alone or in combination with at least one, or alternatively at least two, or alternatively at least three, or alternatively at least four, or alternatively at least five, or alternatively all six of Table 2 alone, or in combination with at least one, or alternatively at least two, or alternatively at least three, or alternatively at least four, or alternatively at least five, or alternatively at least six, or alternatively all seven of Table 3 alone or in combination with at least one, or alternatively at least two, or alternatively at least three, or alternatively at least four, or alternatively at least five, or alternatively at least six, or alternatively at least seven, or alternatively at least eight, or alternatively at least nine, or alternatively at least ten, or alternatively at least eleven or alternatively at least twelve, or alternatively all thirteen of Table 4, then BZ or a biological equivalent thereof in combination with Cetuximab or a biological equivalent thereof, and in some aspects in combination with Irinotecan or a chemical equivalent thereof, is administered or delivered to the patient. This invention also provides the step of administration or delivery of said therapy.

This invention also provides a panel, kit, gene chip or software for patient sampling and performance of the methods of this invention. The kits contain gene chips, slides, software, probes or primers that can be used to amplify and/or for determining the molecular structure or expression level of the genetic markers identified above. In an alternate embodiment, the kit contains antibodies or other polypeptide binding agents that are useful to identify the genetic markers of Tables 1 and/or 2 and/or 3 and/or 4 alone or in combination. Instructions for using the materials to carry out the methods are further provided.

This invention also provides for a panel of genetic markers selected from, but not limited to the genetic polymorphisms identified in Tables 1, 2, 3 or 4 alone or in combination with each other. The panel comprises probes or primers that can be used to amplify and/or for determining the molecular structure of the polymorphisms identified above. The probes or primers can be attached or supported by a solid phase support such as, but not limited to a gene chip or microarray. The probes or primers can be detectably labeled. This aspect of the invention is a means to identify the genotype of a patient sample for the genes of interest identified above.

MODES FOR CARRYING OUT THE INVENTION

Figure 1:
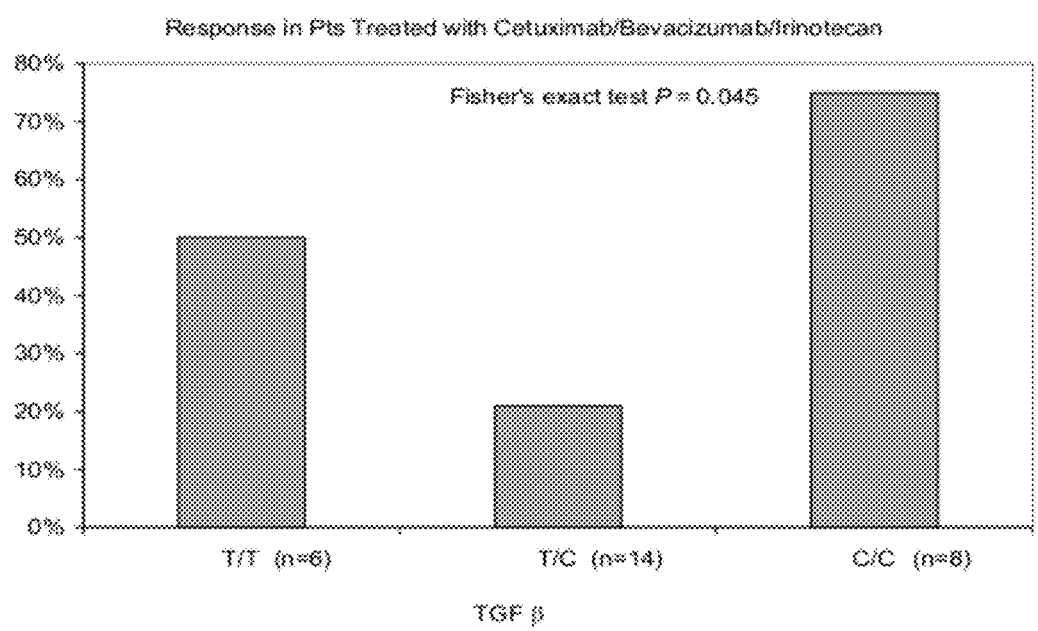
FIG. 1 shows the predictive response to CBI therapy associated with TGF-β (T29C) polymorphism and tumor response. Patients identified as having the genotype C/C or T/T show an increase in response. The letter n equals the number of patients in each group.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Throughout this disclosure, various publications, patents and published patent specifications are referenced by an identifying citation. The disclosures of these publications, patents and published patent specifications are hereby incorporated by reference in their entirety into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook and Russell eds. MOLECULAR CLONING: A LABORATORY MANUAL, $3^{rd}$ edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney $5^{th}$ edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)); MANIPULATING THE MOUSE EMBRyO: A LABORATORY MANUAL $3^{rd}$ edition (Cold Spring Harbor Laboratory Press, Cold Spring Harbor, N.Y. (2002)).

DEFINITIONS

As used herein, certain terms may have the following defined meanings. As used in the specification and claims, the singular form "a," "an" and "the" include singular and plural references unless the context clearly dictates otherwise. For example, the term "a cell" includes a single cell and a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method for the stated purpose. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively the steps and compositions of no significance (consisting essentially of) or alternatively, intending only the stated methods steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

The term "antigen" is well understood in the art and includes substances which are immunogenic. The EGFR is an example of an antigen.

A "native" or "natural" or "wild-type" antigen is a polypeptide, protein or a fragment which contains an epitope and which has been isolated from a natural biological source. It also can specifically bind to an antigen receptor.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention.

The antibodies can be polyclonal or monoclonal and can be isolated from any suitable biological source, e.g., murine, rat, sheep and canine. Additional sources are identified infra.

Bevacizumab is sold under the tradename Avastin by Genentech. It is a humanized monoclonal antibody that binds to and inhibits the biologic activity of human vascular endothelial growth factor (VEGF). Biological equivalent antibodies are identified herein as modified antibodies and those which bind to the same epitope of the antigen, prevent the interaction of VEGF to its receptors (Flt01 and KDR) and produce a substantially equivalent response, e.g., the blocking of endothelial cell proliferation and angiogenesis.

Cetuximab is an example of an anti-EGFR antibody. It is a chimeric human/mouse monoclonal antibody that targets the epidermal growth factor receptor (EGFR). Biological equivalent antibodies are identified herein as modified antibodies and those which bind to the same epitope of the EGFR antigen and produce a substantially equivalent biological response such as, preventing ligand binding of the EGFR, preventing activation of the EGFR receptor and the blocking of the downstream signaling of the EGFR pathway resulting in disrupted cell growth.

In one aspect, the "biological equivalent" means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

Irinotecan (CPT-11) is sold under the tradename of Camptosar®. It is a semi-synthetic analogue of the alkaloid camptothecin, which is activated by hydrolysis to SN-38 and targets topoisomerase I. Chemical equivalents are those that inhibit the interaction of topoisomerase I and DNA to form a catalytically active topoisomerase I-DNA complex. Chemical equivalents inhibit cell cycle progression at G2-M phase resulting in the disruption of cell proliferation.

In one aspect, the "chemical equivalent" means the ability of the chemical to selectively interact with its target protein or fragment thereof as measured by the inactivation of the target protein or other suitable methods. Chemical equivalents include, but are not limited to, those agents with the same pharmaceutically acceptable salt or mixture thereof that interact with and/or inactivate the same target protein as the reference chemical.

The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab')$_2$ fragment, a bivalent fragment comprising two Fab fragments linked by a disulfide bridge at the hinge region; a Fd fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad. Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "antibody variant" is intended to include antibodies produced in a species other than a mouse. It also includes antibodies containing post-translational modifications to the linear polypeptide sequence of the antibody or fragment. It further encompasses fully human antibodies.

The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies, chimeric, recombinant and humanized.

The term "bispecific molecule" is intended to include any agent, e.g., a protein, peptide, or protein or peptide complex, which has two different binding specificities.

The term "multispecific molecule" or "heterospecific molecule" is intended to include any agent, e.g. a protein, peptide, or protein or peptide complex, which has more than two different binding specificities.

The term "heteroantibodies" refers to two or more antibodies, antibody binding fragments (e.g., Fab), derivatives thereof, or antigen binding regions linked together, at least two of which have different specificities.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

A "human monoclonal antibody" refers to antibodies displaying a single binding specificity which have variable and constant regions derived from human germline immunoglobulin sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by heavy chain constant region genes. The IgG isotype consist of four subclasses, IgG1, IgG2, IgG3, and IgG4 each of which having specific activities including the ability to cross into the placenta, act as a complement activator, and to bind to Fc receptors on phahocytic cells. In one embodiment, IgG1 antibodies can cross into the placenta, is the second highest complement activator and has high affinity to bind to Fc receptors on phagocytic cells.

The term "allele", which is used interchangeably herein with "allelic variant", refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The term "genetic marker" refers to an allelic variant of a polymorphic region of a gene of interest and/or the differentially expressed gene of interest. The term "allelic variant of a polymorphic region of the gene of interest" refers to a region of the gene of interest having one of a plurality of nucleotide sequences found in that region of the gene in other individuals.

"Differentially expressed" as applied to a gene, refers to the differential production of the mRNA transcribed from the gene or the protein product encoded by the gene. A differentially expressed gene may be over expressed (high expression) or under expressed (low expression) as compared to the expression level of a normal or control cell, a given patient population or with an internal control. In one aspect, it refers to a differential that is about 1.5 times, or alternatively, about 2.0 times, alternatively, about 2.0 times, alternatively, about 3.0 times, or alternatively, about 5 times, or alternatively, about 10 times, alternatively about 50 times, or yet further alternatively more than about 100 times higher or lower than the expression level detected in a control sample. The term "differentially expressed" also refers to nucleotide sequences in a cell or tissue which are expressed where silent in a control cell or not expressed where expressed in a control cell. In another aspect, expression level is determined by measuring the expression level of a gene of interest for a given patient population, determining the median expression level of that gene for the population, and comparing the expression level of the same gene for a single patient to the median expression level for the given patient population. For example, if the expression level of a gene of interest for the single patient is determined to be above the median expression level of the patient population, that patient is determined to have high expression of the gene of interest. Alternatively, if the expression level of a gene of interest for the single patient is determined to be below the median expression level of the patient population, that patient is determined to have low expression of the gene of interest.

As used herein, the term "gene of interest" intends one or more genes selected from the group consisting of TGF-β, Cyclin D1, UGT1A1, EGFR, FCGRIIIA, XPD, VEGFR2, NRP1, ERCC1, VEGFA, COX-2, IL-8, VEGF, E-cadherin, XRCC1, HIF1α, FCGRIIB, OATPC, NRP1 and GSTP1.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The expression "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype' refers to the detectable outward manifestations of a specific genotype.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or cultural medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "mismatches" refers to hybridized nucleic acid duplexes which are not 100% homologous. The lack of total homology may be due to deletions, insertions, inversions, substitutions or frameshift mutations.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6 ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. HANDBOOK OF FLUORESCENT PROBES AND RESEARCH CHEMICALS (6 ed.). (1996).

In another aspect, the fluorescent label is functionalized to facilitate covalent attachment to a cellular component present in or on the surface of the cell or tissue such as a cell surface marker. Suitable functional groups, including, but are not limited to, isothiocyanate groups, amino groups, haloacetyl groups, maleimides, succi nimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

A "polymorphic gene" refers to a gene having at least one polymorphic region.

When a genetic marker or polymorphism "is used as a basis" for selecting a patient for a treatment described herein, the genetic marker or polymorphism is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits. As would be well understood by one in the art, measurement of the genetic marker or polymorphism in a clinical setting is a clear indication that this parameter was used as a basis for initiating, continuing, adjusting and/or ceasing administration of the treatments described herein.

The term "treating" as used herein is intended to encompass curing as well as ameliorating at least one symptom of the condition or disease. For example, in the case of cancer, likely to respond to treatment includes a reduction in cachexia, increase in survival time, elongation in time to tumor progression, reduction in tumor mass, reduction in tumor burden and/or a prolongation in time to tumor metastasis, each as measured by standards set by the National Cancer Institute and the U.S. Food and Drug Administration for the approval of new drugs. See Johnson et al. (2003) J. Clin. Oncol. 21(7):1404-1411.

A "response" implies any kind of improvement or positive response either clinical or non-clinical such as, but not limited to, measurable reduction in tumor size or evidence of disease or disease progression, complete response, partial response, stable disease, increase or elongation of progression free survival, increase or elongation of overall survival, or reduction in toxicity.

The term "likely to respond" shall mean that the patient is more likely than not to exhibit at least one of the described treatment parameters, identified above, as compared to similarly situated patients.

A "complete response" (CR) to a therapy defines patients with evaluable but non-measurable disease, whose tumor and all evidence of disease had disappeared.

A "partial response" (PR) to a therapy defines patients with anything less than complete response that were simply categorized as demonstrating partial response.

A "responder" intends a patient showing at least a partial response to therapy.

"Stable disease" (SD) indicates that the patient is stable.

"Non-response" (NR) or "Non-responder" to a therapy defines patients whose tumor or evidence of disease has remained constant or has progressed.

"Overall Survival" (OS) intends a prolongation in life expectancy as compared to naïve or untreated individuals or patients.

"Low Risk" intends the median progression free survival would be the longest.

"Intermediate Risk" intends the median progression free survival would be between the low and high risk groups.

"High Risk" intends the median progression free survival would be the shortest.

"Progression free survival" (PFS) or "Time to Tumor Progression" (TTP) indicates the length of time during and after treatment that the cancer does not grow. Progression-free survival includes the amount of time patients have experienced a complete response or a partial response, as well as the amount of time patients have experienced stable disease.

"No Correlation" refers to a statistical analysis showing no relationship between the differentially expressed gene of interest and clinical parameters. The statistical analysis uses the classification and regression tree (CART) method, based on recursive partitioning to examine the associations between mRNA levels of gene of interest and clinical outcome including tumor response, progression-free survival, and overall survival. The cut-off values of mRNA are chosen by the tree analysis to separate patients in terms of probability of response, progressing, or surviving. Additionally, is some aspects of the invention, "No Correlation" refers to a statistical analysis showing no relationship between the allelic variant of a polymorphic region and clinical parameters.

The term "clinical parameters" refers to a reduction or delay in recurrence of the cancer after the initial therapy, time to tumor progression (TTP), decrease in tumor load or size (tumor response or TR), increase median survival time (OS) or decrease metastases.

This invention provides a method for selecting a therapeutic regimen or determining if a certain therapeutic regimen is more likely to treat a malignant condition such as cancer or is the appropriate chemotherapy for that patient than other available chemotherapies. In general, a therapy is considered to "treat" cancer if it provides one or more of the following treatment outcomes: reduce or delay recurrence of the cancer after the initial therapy; time to tumor progression (TTP), decrease in tumor load or size (tumor response or TR), increase median survival time (OS) or decrease metastases. The method is particularly suited to determining which patients will be responsive or experience a positive treatment outcome to adjuvant BZ antibody therapy or an equivalent of such therapy in combination with Cetuximab and in a further aspect Irinotecan or equivalents thereof. These methods are useful to diagnose or predict individual responsiveness to any cancer that has been treatable with these therapies, for example, highly aggressive cancers such as colorectal cancer.

In one embodiment, the adjuvant therapy further comprises radiation therapy or other suitable therapy.

The method comprises screening for a genetic marker identified in Tables 1, 2, 3, or 4 above, and correlating the genetic marker, if present, to the appropriate therapy.

In one embodiment, the invention is a method for determining if a human gastrointestinal cancer patient is likely responsive to therapy comprising, or alternatively consisting essentially or yet further consisting of the administration of anti-VEGF antibody and anti-EGFR antibody based therapy, for example Bevacizumab and Cetuximab or equivalents thereof, by screening a suitable sample isolated from the patient for at least one genetic marker selected from TGF-β (T29C); FCGRIIIA (V158F); XPD (A751C); HIF1-α (C1772T); OATPC (A388G) or FCGRIIB (T232C), wherein for the genetic marker screened, the presence of at least one genetic marker of the group (C/C or T/T) for TGF-β (T29C); (F/F or V/F) for FCGRIIIA (V158F); (A/A or A/C) for XPD (A751C); (C/T or T/T) for HIF1-α (C1772T); (A/A) for OATPC (A388G) or (T/T or T/C) for FCGRIIB (T232C), indicates the patient will likely be responsive to the therapy.

In another embodiment, the invention is a method for determining if a human gastrointestinal cancer patient is likely responsive to therapy comprising, or alternatively consisting essentially or yet further consisting of the administration of anti-VEGF antibody, anti-EGFR antibody and topoisomerase I inhibitor based therapy, for example Bevacizumab, Cetuximab, and Irinotecan therapy, comprising screening a suitable sample isolated from said patient for at least one genetic marker of the group: TGF-β (T29C); Cyclin D1 (A870G); UGT1A1 (UGT1A1*28); EGFR (G497A); ERCC1 (C118T); GSTP1 (V105I); VEGFR2 expression and NRP1 expression; NRP1 expression and ERCC1 expression; EGFR expression; or EGFR expression and VEGFR2 expression, wherein for the genetic marker screened, the presence of at least one genetic marker of the group: (C/C or T/T) for TGF-β (T29C); (A/A or G/G) for Cyclin D1 (A870G); (6/6, 6/7, or 8) for UGT1A1 (UGT1A1*28); (G/G or G/A) for EGFR (G497A); (C/C or T/T) for ERCC1 (C118T); (V/I or I/I) for GSTP1 (V105I); high VEGFR2 expression and low NRP1 expression; high NRP1 expression and low ERCC1 expression; high EGFR expression; or low EGFR expression and high VEGFR2 expression, indicates the patient is likely responsive to said therapy. As described above, high or low expression is relative term. For example, Applicants have determined the following relative expression levels to correlate with clinical outcome: VEGFR2 high expression to be about $\geq 0.65$ and NRP1 low expression to be about <2.885; NRP1 high expression to be about $\geq 1.565$ and ERCC1 low expression to be about <1.2; EGFR high expression to be about $\geq 1.535$; or EGFR low expression to be about <1.535 and VEGFR2 high expression to be about $\geq 0.975$, and are likely to show responsiveness to CBI therapy, wherein responsiveness is any kind of improvement or positive response either clinical or non-clinical selected from, but not limited to, measurable reduction in tumor size or evidence of disease or disease progression, complete response, partial response, stable disease, increase or elongation of progression free survival, increase or elongation of overall survival, or reduction in toxicity.

In one aspect of the above embodiments, a patient's form of response to the described therapy is specifically associated with a genetic polymorphism described herein. These associations are described in Tables 1, 2, 3 and 4 and exemplified in the Experimental Examples 1, 2, and 3. By way of example of this embodiment, the invention is a method for determining if a human metastatic colorectal cancer patient treated with therapy comprising anti-VEGF antibody and anti-EGFR antibody therapy, or equivalents of each thereof, is likely to experience an increase in progression free survival, comprising screening a suitable sample isolated from a the patient for a genetic marker selected from (A/A or A/C) for XPD (A751C); (C/C or T/T) for TGF-β (T29C) or (T/T or T/C) for FCGRIIB (T232C), wherein for the genetic marker identifies the patient as likely to experience an increase in progression free survival. In further aspects of this embodiment, the clinical parameter associated with the genetic marker or profile is selected from reduction in tumor load or size, increase or elongation of time to tumor progression or increase or elongation of overall survival. In yet a further aspect of this embodiment, the therapy comprises an anti-VEGF antibody, an anti-EGFR antibody, and a topoisomerase I inhibitor, or equivalents of each thereof.

In a further aspect of the above embodiments, the gastrointestinal cancer is a metastatic or non-metastatic gastrointestinal cancer selected from the group consisting of rectal cancer, colorectal cancer, colon cancer, gastric cancer, lung cancer, non-small cell lung cancer and esophageal cancer. In another aspect, the gastrointestinal cancer is colorectal cancer. In yet another aspect, the gastrointestinal cancer is metastatic colorectal cancer.

In another embodiment, the invention is a method for treating a human gastrointestinal patient comprising, or alternatively consisting essentially or yet further consisting of administering an effective amount of an anti-VEGF antibody and anti-EGFR antibody based therapy, to a human gastrointestinal patient selected for said therapy based on having at least one genetic marker of the group (C/C or T/T) for TGF-β (T29C); (F/F or V/F) for FCGRIIIA (V158F); (A/A or A/C) for XPD (A751C); (C/T or T/T) for HIF1-α (C1772T); (A/A) for OATPC (A388G); (T/T or T/C) for FCGRIIB (T232C), thereby treating said patient.

In another embodiment, the invention is a method for treating a human gastrointestinal patient comprising, or alternatively consisting essentially or yet further consisting of administering an effective amount of a therapy comprising administration of an effective amount of an anti-VEGF antibody, anti-EGFR antibody and topoisomerase I inhibitor based therapy, to a human gastrointestinal patient selected for said therapy based on having at least one genetic marker of the group (C/C or T/T) for TGF-β (T29C); (A/A or G/G) for Cyclin D1 (A870G); (6/6, 6/7, or 8) for UGT1A1 (UGT1A1*28); (G/G or G/A) for EGFR (G497A); (C/C or T/T) for ERCC1 (C118T); (VII or III) for GSTP1 (V105I); high VEGFR2 expression and low NRP1 expression; high NRP1 expression and low ERCC1 expression; high EGFR expression; or low EGFR expression and high VEGFR2 expression, thereby treating said patient.

In a further aspect of the above methods of treating a human patient, the gastrointestinal cancer is a metastatic or non-metastatic gastrointestinal cancer selected from the group consisting of rectal cancer, colorectal cancer, colon cancer, gastric cancer, lung cancer, non-small cell lung cancer and esophageal cancer. In another aspect, the gastrointestinal cancer is colorectal cancer. In yet another aspect, the gastrointestinal cancer is metastatic colorectal cancer.

In another embodiment, the invention provides for a panel of genetic markers for determining whether a patient is likely responsive to anti-VEGF antibody and anti-EGFR antibody based therapy, the panel comprising a group of primers and/or a probes that identify the genetic markers TGF-β (T29C); FCGRIIIA (V158F); XPD (A751C); HIF1-α (C1772T); OATPC (A388G); or FCGRIIB (T232C).

In another embodiment, the invention provides for a panel of genetic markers for determining whether a patient is likely responsive to anti-VEGF antibody, anti-EGFR antibody and topoisomerase I inhibitor based therapy, the panel comprising a group of primers or probes that identify the genetic markers TGF-β (T29C); Cyclin D1 (A870G); UGT1A1 (UGT1A1*28); EGFR (G497A); ERCC1 (C118T); GSTP1 (V105I); VEGFR2 expression; NRP1 expression; ERCC1 expression; or EGFR expression.

In addition to the methods described herein, the methods described in the following documents can be used to identify the genetic markers of the claimed invention. Methods to identify the polymorphism of TGF-β (T29C) are known in the art and described, for example, in Brazova et al. (2006) Clin. Immunol. 121(3):350-357. CCND1 polymorphism (A870G) is identified by known methods such as those disclosed in Zhang et al. (2006) J. Clin. Oncol. 22(145):3518. UGT1A1 polymorphism (UGT1A1*28) is identified by known methods such as those disclosed in Hasegawa et al. (2004) Clin. Chem. 50:1479-1480. Additionally, UGT1A1*28 polymorphism is also known as (TA/6/7TAA) as described by Lenz et al. (2004) J. Clin. Oncol. 22(13)2519-2521. EGFR polymorphism (G496A) is identified by known method such as those described in Baselga (2005) Nature Clinical Practice Oncology 2:284-285. The XPD polymorphism (A751C) is identified by methods known in the art and described, for example, in Yun et al. (2005) J. Clin. Oncology 22(145):3519. Identification of the genotype FCGRIIIA (V158F) F/F or V/F genotype is described in Yan and Beckman (2005) BioTechniques 39:565-568.

Methods for identification of the Cox-2 genotype G765C are described in Pereira et al. (2006) World J. Gastroenterol 12:5473-5478. EGF genotype A61G is described in Goto et al. (2005) Cancer Epidemiol. Biomarkers Prev. 14:2454-2456. The VEGF allele with +936C/T polymorphism is identified and described in Zhang et al. (2006) Pharmacogenet. Genomics 7:475-483. The IL-8-251T/A allele is identified and described in Zhang et al. (2005) Clin. Colorectal Cancer 5:124-134. Polymorphisms in E-cadherin (-160C/A), ERCC1 (118C/T), XRCC1 (R399Q) and GSTP1 (I105V) are identified as well as methods for their detection and identification are known in the art and reported in U.S. Patent Publications Nos. 2006/0094012 and 2006/0115827.

Methods for determining the levels of the differentially expressed genes of interest, selected from the group of, ERCC1, EGFR, COX2, CCND1, and IL-8 are well known in the art and reported in U.S. Patent Publication No. 2006/0115827. Methods for determining the levels of VEGFR2 are described in Saint-Geniez et al. (2006) Invest. Ophthalmol. Vis. Sci. 47(7):3135-3142. Methods for determining the levels of NRP1 and VEGFA are described in Osada et al. (2004) Anticancer Res. 24(2B):547-52.

Diagnostic Methods

The invention further features diagnostic medicines, which are based, at least in part, on determination of the identity of the polymorphic region or expression level (or both in combination) of the genetic markers identified in Table 1, 2, 3 or 4 above.

For example, information obtained using the diagnostic assays described herein is useful for determining if a subject will respond to cancer treatment of a given type. Based on the prognostic information, a doctor can recommend a therapeutic protocol, useful for treating reducing the malignant mass or tumor in the patient or treat cancer in the individual.

In addition, knowledge of the identity of a particular allele in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. Expression patterns of individual patients can then be compared to the expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

In some aspects, the methods of the present invention require determining expression levels and/or differential expression of the genes of interest identified herein. These methods are not limited by the technique that is used to identify the expression level of the gene of interest. Methods for measuring gene expression are well known in the art and include, but are not limited to, immunological assays, nuclease protection assays, northern blots, in situ hybridization, reverse transcriptase Polymerase Chain Reaction (RT-PCR), Real-Time Polymerase Chain Reaction, expressed sequence tag (EST) sequencing, cDNA microarray hybridization or gene chip analysis, statistical analysis of microarrays (SAM), subtractive cloning, Serial Analysis of Gene Expression (SAGE), Massively Parallel Signature Sequencing (MPSS), and Sequencing-By-Synthesis (SBS). See for example, Carulli et al., (1998) J. Cell. Biochem. 72 (S30-31): 286-296; Galante et al., (2007) Bioinformatics, Advance Access (Feb. 3, 2007).

SAGE, MPSS, and SBS are non-array based assays that determine the expression level of genes by measuring the frequency of sequence tags derived from polyadenylated transcripts. SAGE allows for the analysis of overall gene expression patterns with digital analysis. SAGE does not require a preexisting clone and can used to identify and quantitate new genes as well as known genes. Velculescu et al., (1995) Science 270(5235):484-487; Velculescu (1997) Cell 88(2):243-251.

MPSS technology allows for analyses of the expression level of virtually all genes in a sample by counting the number of individual mRNA molecules produced from each gene. As with SAGE, MPSS does not require that genes be identified and characterized prior to conducting an experiment. MPSS has a sensitivity that allows for detection of a few molecules of mRNA per cell. Brenner et al. (2000) Nat. Biotechnol. 18:630-634; Reinartz et al., (2002) Brief Funct. Genomic Proteomic 1: 95-104.

SBS allows analysis of gene expression by determining the differential expression of gene products present in sample by detection of nucleotide incorporation during a primer-directed polymerase extension reaction.

SAGE, MPSS, and SBS allow for generation of datasets in a digital format that simplifies management and analysis of the data. The data generated from these analyses can be analyzed using publicly available databases such as Sage Genie (Boon et al., (2002) PNAS 99:11287-92), SAGEmap (Lash et al., (2000) Genome Res 10:1051-1060), and Automatic Correspondence of Tags and Genes (ACTG) (Galante (2007), supra). The data can also be analyzed using databases constructed using in house computers (Blackshaw et al. (2004) PLoS Biol, 2:E247; Silva et al. (2004) Nucleic Acids Res 32:6104-6110)).

Over or under expression of a gene, in some cases, is correlated with a genomic polymorphism. The polymorphism can be present in a open reading frame (coded) region of the gene, in a "silent" region of the gene, in the promoter region, or in the 3' untranslated region of the transcript. Methods for determining polymorphisms are well known in the art and include, but are not limited to, the methods discussed below.

Detection of point mutations or additional base pair repeats (as required for the UGT1A1 polymorphism) can be accomplished by molecular cloning of the specified allele and subsequent sequencing of that allele using techniques known in the art. Alternatively, the gene sequences can be amplified directly from a genomic DNA preparation from the tumor tissue using PCR, and the sequence composition is determined from the amplified product. As described more fully below, numerous methods are available for analyzing a subject's DNA for mutations at a given genetic locus such as the gene of interest.

A detection method is allele specific hybridization using probes overlapping the polymorphic site and having about 5, or alternatively 10, or alternatively 20, or alternatively 25, or alternatively 30 nucleotides around the polymorphic region.

In another embodiment of the invention, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the gene of interest prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA.

Alternative amplification methods include: self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques known to those of skill in the art. These detection schemes are useful for the detection of nucleic acid molecules if such molecules are present in very low numbers.

In one embodiment, any of a variety of sequencing reactions known in the art can be used to directly sequence at least a portion of the gene of interest and detect allelic variants, e.g., mutations, by comparing the sequence of the sample sequence with the corresponding wild-type (control) sequence. Exemplary sequencing reactions include those based on techniques developed by Maxam and Gilbert (1997) Proc. Natl. Acad Sci, USA 74:560 or Sanger et al. (1977) Proc. Nat. Acad. Sci, 74:5463. It is also contemplated that any of a variety of automated sequencing procedures can be utilized when performing the subject assays (Biotechniques (1995) 19:448), including sequencing by mass spectrometry (see, for example, U.S. Pat. No. 5,547,835 and International Patent Application Publication Number WO94/16101, entitled DNA Sequencing by Mass Spectrometry by H. Koster; U.S. Pat. No. 5,547,835 and international patent application Publication No. WO 94/21822 entitled "DNA Sequencing by Mass Spectrometry Via Exonuclease Degradation" by H. Koster; U.S. Pat. No. 5,605,798 and International Patent Application No. PCT/US96/03651 entitled DNA Diagnostics Based on Mass Spectrometry by H. Koster; Cohen et al. (1996) Adv. Chromat. 36:127-162; and Griffin et al. (1993) Appl Biochem Bio. 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA Sequencing Employing A Mixed DNA-Polymer Chain Probe" and U.S. Pat. No. 5,571,676 entitled "Method For Mismatch-Directed In Vitro DNA Sequencing."

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) Proc. Natl. Acad. Sci. USA 85:4397; Saleeba et al. (1992) Methods Enzy. 217:286-295. In another embodiment, the control or sample nucleic acid is labeled for detection.

In other embodiments, alterations in electrophoretic mobility are used to identify the particular allelic variant. For example, single strand conformation polymorphism (SSCP) may be used to detect differences in electrophoretic mobility between mutant and wild type nucleic acids (Orita et al. (1989) Proc Natl. Acad. Sci. USA 86:2766; Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al. (1989) Proc. Natl. Acad. Sci. USA 86:6230 and Wallace et al. (1979) Nucl. Acids Res. 6:3543). Such allele specific oligonucleotide hybridization techniques may be used for the detection of the nucleotide changes in the polylmorphic region of the gene of interest. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell. Probes 6:1).

In another embodiment, identification of the allelic variant is carried out using an oligonucleotide ligation assay (OLA), as described, e.g., in U.S. Pat. No. 4,998,617 and in Landegren, U. et al. Science 241:1077-1080 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson et al. (1990) Proc. Natl. Acad. Sci. (U.S.A.) 87:8923-8927). In this method, PCR is used to achieve the exponential amplification of target DNA, which is then detected using OLA.

Several techniques based on this OLA method have been developed and can be used to detect the specific allelic variant of the polymorphic region of the gene of interest. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. (1996) Nucleic Acids Res. 24: 3728, OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting the single nucleotide polymorphism in the gene of interest. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site. Cohen et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet et al. (PCT Appln. No. 92/15712). This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet et al. supra, is preferably a heterogeneous phase assay, in which the primer or the target molecule is immobilized to a solid phase.

Recently, several primer-guided nucleotide incorporation procedures for assaying polymorphic sites in DNA have been described (Komher et al. (1989) Nucl. Acids. Res. 17:7779-7784; Sokolov (1990) Nucl. Acids Res. 18:3671; Syvanen et al. (1990) Genomics 8:684-692; Kuppuswamy et al. (1991) Proc. Natl. Acad. Sci. (U.S.A.) 88:1143-1147; Prezant et al. (1992) Hum. Mutat. 1:159-164; Ugozzoli et al. (1992) GATA 9:107-112; Nyren et al. (1993) Anal. Biochem. 208:171-175). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen et al. (1993) Amer. J. Hum. Genet. 52:46-59).

If the polymorphic region is located in the coding region of the gene of interest, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art.

Antibodies directed against wild type or mutant peptides encoded by the allelic variants of the gene of interest may also be used in disease diagnostics and prognostics. Such diagnostic methods, may be used to detect abnormalities in the level of expression of the peptide, or abnormalities in the structure and/or tissue, cellular, or subcellular location of the peptide. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook and Russel (2001) supra. The protein detection and isolation methods employed herein can also be such as those described in Harlow and Lane (1999) supra. This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of the peptides or their allelic variants. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the subject polypeptide, but also its distribution in the examined tissue. Using the present invention, one of ordinary skill will readily perceive that any of a wide variety of histological methods (such as staining procedures) can be modified in order to achieve such in situ detection.

In one aspect the invention provided for a panel of genetic markers selected from, but not limited to the genetic polymorphisms above. The panel comprises probes or primers that can be used to amplify and/or for determining the molecular structure of the polymorphisms identified above. The probes or primers can be attached or supported by a solid phase support such as, but not limited to a gene chip or microarray. The probes or primers can be detectably labeled. This aspect of the invention is a means to identify the genotype of a patient sample for the genes of interest identified above. In one aspect, the methods of the invention provided for a means of using the panel to identify or screen patient samples for the presence of the genetic marker identified herein. In one aspect, the various types of panels provided by the invention include, but are not limited to, those described herein. In one aspect, the panel contains the above identified probes or primers as wells as other, probes or primers. In an alternative aspect, the panel includes one or more of the above noted probes or primers and others. In a further aspect, the panel consist only of the above-noted probes or primers.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid described herein, which may be conveniently used, e.g., to determine whether a subject has or is at risk of developing disease such as colorectal cancer.

Sample nucleic acid for use in the above-described diagnostic and prognostic methods can be obtained from any cell type or tissue of a subject. For example, a subject's bodily fluid (e.g. blood) can be obtained by known techniques (e.g., venipuncture). Alternatively, nucleic acid tests can be performed on dry samples (e.g., hair or skin) Fetal nucleic acid samples can be obtained from maternal blood as described in International Patent Application No. WO91/07660 to Bianchi. Alternatively, amniocytes or chorionic villi can be obtained for performing prenatal testing.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures (see, for example, Nuovo (1992) "PCR 1N SITU HYBRIDIZATION: PROTOCOLS AND APPLICATIONS", Raven Press, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

The invention described herein relates to methods and compositions for determining and identifying the allele present at the gene of interest's locus. This information is useful to diagnose and prognose disease progression as well as select the most effective treatment among treatment options. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook and Russel (2001) supra. A probe can be a polynucleotide of any length suitable for selective hybridization to a nucleic acid containing a polymorphic region of the invention. Length of the probe used will depend, in part, on the nature of the assay used and the hybridization conditions employed.

In one embodiment of the invention, probes are labeled with two fluorescent dye molecules to form so-called "molecular beacons" (Tyagi and Kramer (1996) Nat. Biotechnol. 14:303-8). Such molecular beacons signal binding to a complementary nucleic acid sequence through relief of intramolecular fluorescence quenching between dyes bound to opposing ends on an oligonucleotide probe. The use of molecular beacons for genotyping has been described (Kostrikis (1998) Science 279:1228-9) as has the use of multiple beacons simultaneously (Marras (1999) Genet. Anal. 14:151-6). A quenching molecule is useful with a particular fluorophore if it has sufficient spectral overlap to substantially inhibit fluorescence of the fluorophore when the two are held proximal to one another, such as in a molecular beacon, or when attached to the ends of an oligonucleotide probe from about 1 to about 25 nucleotides.

Labeled probes also can be used in conjunction with amplification of a polymorphism. (Holland et al. (1991) Proc. Natl. Acad. Sci. 88:7276-7280). U.S. Pat. No. 5,210,015 by Gelfand et al. describe fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule—quencher molecule pair that specifically anneals to a region of a target polynucleotide containing the polymorphism.

Probes can be affixed to surfaces for use as "gene chips" or "microarray." Such gene chips or microarrays can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarray" and similar technologies are know in the art. Examples of such include, but are not limited to LabCard (ACLARA Bio Sciences Inc.); GeneChip (Affymetrix, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarraying system that can dispense from 12 to 64 spots onto multiple glass slides (Intelligent Bio-Instruments); Molecular Biology Workstation and NanoChip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu Rev. Biomed. Eng. 4:129-153. Examples of "Gene chips" or a "microarray" are also described in US Patent Publ. Nos.: 2007-0111322, 2007-0099198, 2007-0084997, 2007-0059769 and 2007-0059765 and U.S. Pat. Nos. 7,138,506, 7,070,740, and 6,989,267.

In one aspect, "gene chips" or "microarrays" containing probes or primers for genes of Tables 1, 2, 3 or 4 alone or in combination are prepared. A suitable sample is obtained from the patient extraction of genomic DNA, RNA, or any combination thereof and amplified if necessary. The DNA or RNA sample is contacted to the gene chip or microarray panel under conditions suitable for hybridization of the gene(s) of interest to the probe(s) or primer(s) contained on the gene chip or microarray. The probes or primers may be detectably labeled thereby identifying the polymorphism in the gene(s) of interest. Alternatively, a chemical or biological reaction may be used to identify the probes or primers which hybridized with the DNA or RNA of the gene(s) of interest. The genotypes of the patient is then determined with the aid of the aforementioned apparatus and methods.

Nucleic Acids

In one aspect, the nucleic acid sequences of the gene's allelic variants, or portions thereof, can be the basis for probes or primers, e.g., in methods for determining the identity of the allelic variant of a polymorphic region(s). Thus, they can be used in the methods of the invention to determine which therapy is most likely to treat an individual's cancer.

The methods of the invention can use nucleic acids isolated from vertebrates. In one aspect, the vertebrate nucleic acids are mammalian nucleic acids. In a further aspect, the nucleic acids used in the methods of the invention are human nucleic acids.

Primers for use in the methods of the invention are nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes for use in the methods of the invention are nucleic acids which hybridize to the region of interest and which are not further extended. For example, a probe is a nucleic acid which hybridizes to the polymorphic region of the gene of interest, and which by hybridization or absence of hybridization to the DNA of a subject will be indicative of the identity of the allelic variant of the polymorphic region of the gene of interest. Primers and Probes useful in the methods described herein are found in Tables and 6.

TABLE 5

Probe and Primer Sequences for Determining Gene Expression Levels

| Gene | Forward Primer (5'-3') (SEQ ID NO.) | Reverse Primer (5'-3') (SEQ ID NO.) | Taqman Probe (5'-3') (SEQ ID NO.) |
|---|---|---|---|
| Beta-actin | GAGCGCGGCTACAGCTT (1) | TCCTTAATGTCACGCACGATTT (2) | ACCACCACGGCCGAGCGG (3) |
| VEGFR2 | CCTGTGGCTCTGCGTGGA (4) | CTGAGCCTGGGCAGATCAAG (5) | CACTAGGCAAACCCACAGAGGCGGC (6) |
| NRP1 | CCGCCTGAACTACCCTGAG (7) | GCAGAAGGCCCAAGTCTACC (8) | TCCCGGAGAGGATTCCTACCGA (9) |
| ERCC1 | GGGAATTTGGCGACGTAATTC (10) | GCGGAGGCTGAGGAACAG (11) | CACAGGTGCTCTGGCCCAGCACATA (12) |
| VEGFA | AGTGGTCCCAGGCTGCAC (13) | TCCATGAACTTCACCACTTCGT (14) | ATGGCAGAAGGAGGAGGGCAGAATCA (15) |
| EGFR | TGCGTCTCTTGCCGGAAT (16) | GGCTCACCCTCCAGAAGCTT (17) | ACGCATTCCCTGCCTCGGCTG (18) |
| COX-2 | GCTCAACATGATGTTTGCATTC (19) | GCTGGCCCTCGCTTATGA (20) | TGCCCAGCACTTCACGCATCAGTT (21) |
| Cyclin D1 | TGCATGTTCGTGGCCTCTAA (22) | TCGGTGTAGATGCACAGCTTCT (23) | AAGGAGACCATCCCCCTGACGGC (24) |
| IL-8 | CAGCTCTGTGTGAAGGTGCAGTT (25) | GGGTGGAAAGGTTTGGAGTATGTC (26) | TGCACTGACATCTAAGTTCTTTAGCACTCCTTGGC (27) |

TABLE 6

Primer Sequences, Annealing Temperatures and Restriction Enzymes for Determining Polymorphisms

| Gene | Forward Primer (5'-3') | Reverse Primer (5'-3') | Enzyme | Annealing |
|---|---|---|---|---|
| TGF-β T29C | TGCCGCCCTCCGGGCTGCGGCTGCGGC (28) | TCTTGCAGGTGGATAGTCCCGCGGTCGG (29) | HaeIII | 60 |
| FCGRIIIA V158F | CTGAAGACACATTTTTACTCCCAAAC (30) | TCCAAAAGCCACACTCAAAGAC (31) | Sequence | 64 |
| XPD A751C | CCTCTCCCTTTCCTCTGTTC (33) | CAGGTGAGGGGACATCT (33) | MboII | 60 |

TABLE 6-continued

Primer Sequences, Annealing Temperatures and Restriction Enzymes for Determining Polymorphisms

| Gene | Forward Primer (5'-3') | Reverse Primer (5'-3') | Enzyme | Annealing |
|---|---|---|---|---|
| HIF1-α C1772T | CCCAATGGATGATGACTTCC (35) | AGTGGTGGCATTAGCAGTAGG (35) | Tsp-45 I | 60 |
| OATPC A388G | GCAAAATGTTTAATTCAGTGATGTTC (37) | TCCCACTATCTCAGGTGATGC (37) | NA | 55 |
| FCGRIIB T232C | CTAAGAGGAGCCCTTCCCTATGT (39) | AATACGGGCCTAGATCTGAATGTG (39) | Sequence | 54 |
| Cyclin D1 A870G | GTGAAGTTCATTTCCAATCCGC (41) | GGACATCACCCTCACTTAC (41) | ScrF I | 55° |
| UGT1A1 UGT1A1*28 | GTCACGTGACACAGTCAAAC (43) | TTTGCTCCTGCCAGAGGTT (43) | Sequence | 55 |
| EGFR G497A | TGCTGTGACCCACTCTGTCT (45) | CCAGAAGGTTGCACTTGTCC (45) | Bst-NI | 59° |
| ERCC1 C-118T | GCAGAGCTCACCTGAGGAAC (47) | GAGGTGCAAGAAGAGGTGGA (47) | BsrDI | 60 |
| GSTP V105I | ACCCCAGGGCTCTATGGGAA (49) | TGAGGGCACAAGAAGCCCCT (49) | BsmAI | 60 |
| VEGF C + 936T | AAGGAAGAGGAGACT CTGCGCAGAGC (51) | TAAATGTATGTATGTGGG TGGGTGTGTCTACAGG (51) | Nla III | 60° |
| IL8 T-251A | TTGTTCTAACACCTG CCACTCT (53) | GGCAAACCTGAGTC TCACA (53) | Mfe I | 60° |
| COX-2 G765C | CCGCTTCCTTTGTCCATCAG (54) | GGCTGTATATCTGCTCTATATGC (55) | Aci I | 55° |
| E-cadherin C-160A | TCCCAGGTCTTAGTGAGCCA (56) | ACGACTAACCGACACCGG (57) | AflIII | 60 |
| XRCC1 R399Q | TAAGGAGTGGGTGCCGGACTGTC (58) | AGTAGTCTGCTGGCTCTGG (59) | MspI | 60 |

In one embodiment, primers comprise a nucleotide sequence which comprises a region having a nucleotide sequence which hybridizes under stringent conditions to about: 6, or alternatively 8, or alternatively 10, or alternatively 12, or alternatively 25, or alternatively 30, or alternatively 40, or alternatively 50, or alternatively 75 consecutive nucleotides of the gene of interest.

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified.

Yet other preferred primers of the invention are nucleic acids which are capable of selectively hybridizing to an allelic variant of a polymorphic region of the gene of interest. Thus, such primers can be specific for the gene of interest sequence, so long as they have a nucleotide sequence which is capable of hybridizing to the gene of interest.

The probe or primer may further comprises a label attached thereto, which, e.g., is capable of being detected, e.g. the label group is selected from amongst radioisotopes, fluorescent compounds, enzymes, and enzyme co-factors.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

The nucleic acids used in the methods of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane. See, e.g., Letsinger et al., (1989) Proc. Natl. Acad. Sci. U.S.A. 86:6553-6556; Lemaitre et al., (1987) Proc. Natl. Acad. Sci. 84:648-652; and PCT Publication No. WO 88/09810, published Dec. 15, 1988), hybridization-triggered cleavage agents, (see, e.g., Krol et al., (1988) BioTechniques 6:958-976) or intercalating agents (see, e.g., Zon (1988) Pharm. Res. 5:539-549. To this end, the nucleic acid used in the methods of the invention may be conjugated to another molecule, e.g., a peptide, hybridization triggered cross-linking agent, transport agent, hybridization-triggered cleavage agent, etc.

The isolated nucleic acids used in the methods of the invention can also comprise at least one modified sugar moiety selected from the group including but not limited to arabinose, 2-fluoroarabinose, xylulose, and hexose or, alternatively, comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The nucleic acids, or fragments thereof, to be used in the methods of the invention can be prepared according to methods known in the art and described, e.g., in Sambrook and Russel (2001) supra. For example, discrete fragments of the DNA can be prepared and cloned using restriction enzymes. Alternatively, discrete fragments can be prepared using the Polymerase Chain Reaction (PCR) using primers having an appropriate sequence under the manufacturer's conditions, (described above).

Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988) Nucl. Acids Res. 16:3209, methylphosphonate oligonucleotides can be prepared by use of controlled pore glass polymer supports. Sarin et al. (1988) Proc. Natl. Acad. Sci. U.S.A. 85:7448-7451.

Methods of Treatment

The invention further provides methods of treating subjects having solid malignant tissue mass or tumor selected from rectal cancer, colorectal cancer, (including metastatic CRC), colon cancer, gastric cancer, lung cancer (including non-small cell lung cancer) and esophageal cancer. In one embodiment, the method comprises (a) determining the identity of the allelic variant as identified herein; and (b) administering to the subject an effective amount of a compound or therapy (e.g., BZ antibody, mimetic or biological equivalent thereof). This therapy can be combined with other suitable therapies or treatments.

The antibodies and compositions are administered or delivered in an amount effective to treat the cancer and by any suitable means and with any suitable formulation as a composition and therefore includes a carrier such as a pharmaceutically acceptable carrier. Accordingly, a formulation comprising an antibody or biological equivalent thereof is further provided herein. The formulation can further comprise one or more preservatives or stabilizers. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

The antibodies or biological equivalents thereof can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myo-inositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in Montvale (1998) PHYSICIAN'S DESK REFERENCE, $52^{nd}$ ed., Medical Economics.

An "effective amount" is an amount sufficient to effect beneficial or desired results. An effective amount can be administered in one or more administrations, applications or dosages.

The invention provides an article of manufacture, comprising packaging material and at least one vial comprising a solution of at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

The antibody or equivalent thereof is prepared to a concentration includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

The formulations of the present invention can be prepared by a process which comprises mixing at least one antibody or biological equivalent and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include pen-injector devices for delivery of a solution such as BD Pens, BD Autojectore, Humaject®, NovoPen®, B-D®Pen, AutoPen®, and Opti-Pen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

Various delivery systems are known and can be used to administer a therapeutic agent of the invention, e.g., encapsulation in liposomes, microparticles, microcapsules, expression by recombinant cells, receptor-mediated endocytosis. See e.g., Wu and Wu (1987) J. Biol. Chem. 262:4429-4432 for construction of a therapeutic nucleic acid as part of a retroviral or other vector, etc. Methods of delivery include but are not limited to intra-arterial, intra-muscular, intravenous, intranasal and oral routes. In a specific embodiment, it may be desirable to administer the pharmaceutical compositions of the invention locally to the area in need of treatment; this may be achieved by, for example, and not by way of limitation, local infusion during surgery, by injection or by means of a catheter.

In certain embodiments, an effective amount of Irinotecan or a chemical equivalent is administered to the patient. Compositions comprising these compounds can be prepared in accordance with known formulation techniques to provide a composition suitable for oral, topical, transdermal, rectal, inhalation, or parenteral (intravenous, intramuscular, or intraperitoneal) administration, and the like. Detailed guidance for preparing compositions of the invention are found by reference to the 18$^{th}$ or 19$^{th}$ Edition of REMINGTON'S PHARMACEUTICAL SCIENCES, Mack Publishing Co., Easton, Pa. 18040.

Irinotecan or a chemical equivalent is administered in a therapeutically effective amount sufficient to treat cancer in a subject and may contain from about 1.0 to 1000 mg of compound, for example about 1, 5, 10, 15, 20, 25, 50, 75, 100, 125, 150, 175, 200, 225, 250, 275, 300, 325, 350, 375, 400, 425, 450, 475, to 500 mg.

Irinotecan or a chemical equivalent can be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will contain about 50 to about 500 mg.

Irinotecan or a chemical equivalent may deliver the compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. An alternative composition according to the current invention are prepared so that an oral dosage unit form contains between about 5 to about 50% by weight (% w) in dosage units weighing between 50 and 1000 mg.

The suitable formulation of an oral dosage unit of Irinotecan or a chemical equivalent may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of REMINGTON: THE SCIENCE AND PRACTICE OF PHARMACY, Mack Printing Company, Easton, Pa. See particularly chapters 91-93 for a fuller discussion.

Irinotecan or a chemical equivalent may be administered parenterally, e.g., intravenously, intramuscularly, intravenously, subcutaneously, or interperitonically. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of Irinotecan or a chemical equivalent may be prepared in suitable diluents such as water, ethanol, glycerol, liquid polyethylene glycol(s), various oils, and/or mixtures thereof, and others known to those skilled in the art.

The pharmaceutical forms of Irinotecan or a chemical equivalent suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized. Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

Usefully, Irinotecan or a chemical equivalent of the invention is solubilized in liposomes. The liposomes may include, for example, lipids such as cholesterol, phospholipids, or micelles comprised of surfactant such as, for example, sodium dodecylsulfate, octylphenolpolyoxyethylene glycol, or sorbitan mono-oleate. Typically, the compound of the invention binds to the lipid bilayer membrane of the liposome with high affinity. The liposome bound prodrug can preferably intercalate between the acyl chains of the lipid. The lactone ring of the camptothecin-derivative, membrane-bound compound of the invention is thereby removed from the aqueous environment inside and outside of the liposome and further protected from hydrolysis. Since the liposome-bound drug is protected from hydrolysis, the antitumor activity of the drug is preserved. If Irinotecan or a chemical equivalent of the invention has a lower affinity for the liposome membrane and thus disassociates from the liposome membrane to reside in the interior of liposome, the pH of the interior of the liposomes may be reduced thereby preventing hydrolysis of such compound of the invention.

U.S. Pat. No. 6,096,336 provides further guidance for preparing liposomal compositions useful in this invention.

In one aspect of the invention, a chemical equivalent of Irinotecan (a topoisomerase I inhibitor) selected from the group of, but not limited to, Campothecine derivatives including CPT-11/Irinotecan, SN-38, APC, NPC, camptothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier Y. (2006) Nat. Rev. Cancer 6(10):789-802 and US Patent Publ. No. 2005/0250854; Protoberberine alkaloids and derivatives thereof including berberrubine and coralyne as described in Li et al. (2000) Biochemistry 39(24):7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11(8): 1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-125, Crow et al. (1994) J. Med. Chem. 37(19):3191-3194, and (Crespi et al. (1986) Biochem. Biophys. Res. Commun. 136(2):521-8, can be used in combination therapy with the antibody based chemotherapy described above to treat patients identified as having the appropriate genetic markers.

In another aspect of the invention, dual topoisomerase I and II inhibitors selected from the group of, but not limited to, Saintopin and other Naphthecenediones, DACA and other Acridine-4-Carboxamindes, Intoplicine and other Benzopyridoindoles, TAS-103 and other 7H-indeno[2,1-c]Quinoline-7-ones, Pyrazoloacridine, XR 11576 and other Benzophenazines, XR 5944 and other Dimeric compounds, 7-Oxo-7H-dibenz[f,ij]Isoquinolines and 7-oxo-7H-benzo[e] Perimidines, and Anthracenyl-amino Acid Conjugates as described in Denny and Baguley (2003) Curr. Top. Med. Chem. 3(3):339-353, can be used in combination therapy with the antibody based chemotherapy described above to treat patients identified as having the appropriate genetic markers.

The agents identified herein as effective for their intended purpose can be administered to subjects or individuals identified by the methods herein as suitable for the therapy, Therapeutic amounts can be empirically determined and will vary with the pathology being treated, the subject being treated and the efficacy and toxicity of the agent.

Biological Equivalent Antibodies and Therapies

In one aspect, after determining that antibody therapy alone or in combination with other suitable therapy is likely to provide a benefit to the patient, the invention further comprises administration of a BZ or Cetuximab antibody, fragment, variant or derivative thereof. The antibodies of this invention are monoclonal antibodies, although in certain aspects, polyclonal antibodies can be utilized. They also can be functional fragments, antibody derivatives or antibody variants. They can be chimeric, humanized, or totally human. A functional fragment of an antibody includes but is not limited to Fab, Fab', Fab2, Fab'2, and single chain variable regions. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. So long as the fragment or derivative retains specificity of binding or neutralization ability as the antibodies of this invention it can be used. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific.

The antibodies also are characterized by their ability to specifically bind to an equivalent epitope. The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

Polyclonal antibodies of the invention can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammals serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antiben depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709,659; 6,656,746; 6,322,788; 5,686,073; and 5,670,153.

The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., www.atcc.org, www.lifetech.com., last accessed on Nov. 26, 2007, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

In one embodiment, the antibodies described herein can be generated using a Multiple Antigenic Peptide (MAP) system. The MAP system utilizes a peptidyl core of three or seven radially branched lysine residues, on to which the antigen peptides of interest can be built using standard solid-phase chemistry. The lysine core yields the MAP bearing about 4 to 8 copies of the peptide epitope depending on the inner core that generally accounts for less than 10% of total molecular weight. The MAP system does not require a carrier protein for conjugation. The high molar ratio and dense packing of multiple copies of the antigenic epitope in a MAP has been shown to produce strong immunogenic response. This method is described in U.S. Pat. No. 5,229,490 and is herein incorporated by reference in its entirety.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsreid/Planegg, Del.), Biovation (Aberdeen, Scotland, UK) Bioinvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al., (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al., (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol). 17:887-892; Babcook et al., Proc. Natl. Acad. Sci. USA (1996) 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; Kenny et al. (1995) Bio/Technol. 13:787-790); and B-cell selection (Steenbakkers et al. (1994) Molec. Biol. Reports 19:125-134).

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody variant" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method, such as but not limited to those described in U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. See for example, Russel et al. (2000) Infection and Immunity April:1820-1826; Gallo et al. (2000) European J. Immun. 30:534-540; Green (1999) J. Immun. Methods 231:11-23; Yang et al. (1999) J. Leukocyte Biology 66:401-410; Yang, X-D (1999) Cancer Research 59(6):1236-1243; Jakobovits (1998) Advanced Drug Delivery Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold, R. (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4): 247-260; Jakobovits (1993) Nature 362(6417):255-258; Jakobovits et al. (1993) Proc. Natl. Acad. Sci. USA 90(6): 2551-2555; Kucherlapati et al. U.S. Pat. No. 6,075,181.

Human monoclonal antibodies can also be produced by a hybridoma which includes a B cell obtained from a transgenic nonhuman animal, e.g., a transgenic mouse, having a genome comprising a human heavy chain transgene and a light chain transgene fused to an immortalized cell.

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) SEQUENCES OF PROTEINS OF IMMUNOLOGICAL INTEREST, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain (VH-VL). See for example, EP 404,097; WO 93/11161; and Hollinger et al., (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.

The term "antibody derivative" further includes "linear antibodies". The procedure for making this is known in the art and described in Zapata et al. (1995) Protein Eng. 8(10): 1057-1062. Briefly, these antibodies comprise a pair of tandem Fd segments (V-C1-VH-C1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

If a monoclonal antibody being tested binds with protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski, et al. (1985) Proc. Natl. Acad. Sci. USA 82:8653 or Spira, et al. (1984) J. Immunol. Methods 74:307.

The isolation of other hybridomas secreting monoclonal antibodies with the specificity of the monoclonal antibodies of the invention can also be accomplished by one of ordinary skill in the art by producing anti-idiotypic antibodies. Herlyn, et al. (1986) Science 232:100. An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

In some aspects of this invention, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

Antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99}$m Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from Chinese cobra (naj a naja atra), and gelonin (a plant toxin); ribosome inactivating proteins from plants, bacteria and fungi, such as restrictocin (a ribosome inactivating protein produced by *Aspergillus* restrictus), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

The antibodies for use in this therapy can be further modified. The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis. See generally, Hermanson, G. T., BIOCONJUGATE TECHNIQUES, Academic Press: San Diego, Calif. (1996).

In one aspect of the invention, biological equivalents of Cetuximab (an anti-EGFR antibody) selected from the group of, but not limited to, Panitumumab (ABX-EGF) as described in US Patent Publ. Nos.: 2005/0272083 and 2004/0033543; TheraCIM, EMD 72000, and MDX447 as described in US Patent Publ. No.: 2007/0014792; or H425 and C225 as described in US Patent Publ. Nos. 2006/0610561, 20050175611, and 2004/0131611, can be used to treat patients identified as having the appropriate genetic polymorphisms.

The Bevacizumab and/or Cetuximab antibodies can be further modified. The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis. See generally, Hermanson BIOCONJUGATE TECHNIQUES, Academic Press: San Diego, Calif. (1996).

In one aspect of the invention, biological equivalents of Bevacizumab (an anti-VEGF antibody) selected from the group of, but not limited to, antibody A4.6.1 and derivatives thereof as described in US Patent Publ. Nos.: 2007/0071749, 20070071748, 2007/0071718, and 2007/002599; any one of the series of humanized and variant anti-VEGF antibodies described in US Patent Publ. Nos. 2005/0112126, 2003/0190317, and 2002/0032315; or antibody 2C3 and derivatives thereof described in US Patent Publ. No. 2002/0119153, can be used in combination therapy with the anti-EGFR based chemotherapy and in some aspects topoisomerase I inhibitor based chemotherapy described above to treat patients identified as having the appropriate genetic markers.

In one aspect of the invention, biological equivalents of Cetuximab (an anti-EGFR antibody) selected from the group of, but not limited to, Panitumumab (ABX-EGF) as described in US Patent Publ. Nos.: 2005/0272083 and 2004/0033543; TheraCIM, EMD 72000, and MDX447 as described in US Patent Publ. No.: 2007/0014792; or H425 and C225 as described in US Patent Publ. Nos. 2006/0610561, 20050175611, and 2004/0131611, can be used in combination therapy with the anti-VEGF based chemotherapy and in some aspects topoisomerase I inhibitor based chemotherapy described above to treat patients identified as having the appropriate genetic markers.

Also provided is a medicament comprising an effective amount of a therapy as described herein for treatment of a human cancer patient having one or more predictive polymorphism or genetic markers as identified in Table 1, 2, 3, 4 or the experimental examples.

Kits

As set forth herein, the invention provides diagnostic methods for determining the type of allelic variant of a polymorphic region present in the gene of interest or the expression level of a gene of interest. In some embodiments, the methods use probes or primers comprising nucleotide sequences which are complementary to the polymorphic region of the gene of interest. Accordingly, the invention provides kits for performing these methods as well as instructions for carrying out the methods of this invention such as collecting tissue and/or performing the screen, and/or analyzing the results, and/or administration of an effective amount of the therapies described above.

In an embodiment, the invention provides a kit for determining whether a subject responds to cancer treatment or alternatively one of various treatment options. The kits contain one of more of the compositions described above and instructions for use. As an example only, the invention also provides kits for determining response to cancer treatment containing a first and a second oligonucleotide specific for the polymorphic region of the gene. Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, and preferably less than 1 kb from the polymorphism. Specific oligonucleotides are capable of hybridizing to a sequence, and under suitable conditions will not bind to a sequence differing by a single nucleotide.

The kit can comprise at least one probe or primer which is capable of specifically hybridizing to the polymorphic region of the gene of interest and instructions for use. The kits preferably comprise at least one of the above described nucleic acids. Preferred kits for amplifying at least a portion of the gene of interest comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the preferred surface is silica or glass. In another embodiment, the surface is a metal electrode.

Yet other kits of the invention comprise at least one reagent necessary to perform the assay. For example, the kit can comprise an enzyme. Alternatively the kit can comprise a buffer or any other necessary reagent.

Conditions for incubating a nucleic acid probe with a test sample depend on the format employed in the assay, the detection methods used, and the type and nature of the nucleic acid probe used in the assay. One skilled in the art will recognize that any one of the commonly available hybridization, amplification or immunological assay formats can readily be adapted to employ the nucleic acid probes for use in the present invention. Examples of such assays can be found in Chard (1986) AN INTRODUCTION TO RADIOIMMUNOASSAY AND RELATED TECHNIQUES Elsevier Science Publishers, Amsterdam, The Netherlands; Bullock et al. TECHNIQUES IN IMMUNOCYTOCHEMISTRY Academic Press, Orlando, Fla. Vol. 1 (1982), Vol. 2 (1983), Vol. 3 (1985); Tijssen, PRACTICE AND THEORY OF IMMUNOASSAYS: LABORATORY TECHNIQUES IN BIOCHEMISTRY AND MOLECULAR BIOLOGY, Elsevier Science Publishers, Amsterdam, The Netherlands (1985).

The test samples used in the diagnostic kits include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

The kits can include all or some of the positive controls, negative controls, reagents, primers, sequencing markers, probes and antibodies described herein for determining the subject's genotype in the polymorphic region or the expression levels of the gene of interest.

As amenable, these suggested kit components may be packaged in a manner customary for use by those of skill in the art. For example, these suggested kit components may be provided in solution or as a liquid dispersion or the like.

Other Uses for the Nucleic Acids of the Invention

The identification of the allele of the gene of interest can also be useful for identifying an individual among other individuals from the same species. For example, DNA sequences can be used as a fingerprint for detection of different individuals within the same species. Thompson and Thompson, Eds., (1991) GENETICS IN MEDICINE, W B Saunders Co., Philadelphia, Pa. This is useful, e.g., in forensic studies.

The invention now being generally described, it will be more readily understood by reference to the following examples which are included merely for purposes of illustration of certain aspects and embodiments of the present invention, and are not intended to limit the invention.

EXPERIMENTAL EXAMPLES

For the purpose of illustration only, peripheral blood sample can be collected from each patient, and genomic DNA can be extracted from white blood cells using the QiaAmp kit (Qiagen, Valencia, Calif.).

Example 1

Background Phase II CBI VS CB trial has shown that Bevacizumab added the efficacy of cetuximab and cetuximab/irinotecan in irinotecan-refractory Bevacizumab-naïve CRC patients. Germline polymorphisms involved in angiogenesis (VEGF, IL-8, TGF-β), the EGFR pathway (EGFR, COX-2, E-cadherin), DNA repair (ERCC1, XRCC1, XPD) and drug metabolism pathway (GSTP1, UGT1A1) were tested to evaluate their association with clinical outcome.

Methods Blood samples for 65 out of 81 patients (abbreviated as "pts") enrolled in the BOND 2 study were tested for polymorphisms, and the results from these 65 pts are reported in this analysis (44 men, 21 women, median age 58 years (range 24-86)). Pts received either with Cetuximab/BZ/Irinotecan "CBI" (n=31) (Arm A) or with Cetuximab and BZ "CB" (n=34) (Arm B). In Arm A, 12 pts (43%) had PR, the median time to progression was 7.1 months, and the median survival was 18.0 months. In Arm B, 9 pts (27%) had PR, the median time to progression was 4.6 months, and the median survival was 10.3 months. Germline DNA was extracted from peripheral blood, PCR-RFLP based technique was used to determine polymorphisms. Univariate analysis (Fisher's exact test for response; log-rank test for TTP and OS) was performed to examine associations between polymorphisms and clinical outcome. Probes and primers for this analysis are known in the art as described herein, examples of which are provided in Table 5.

Figure 2:
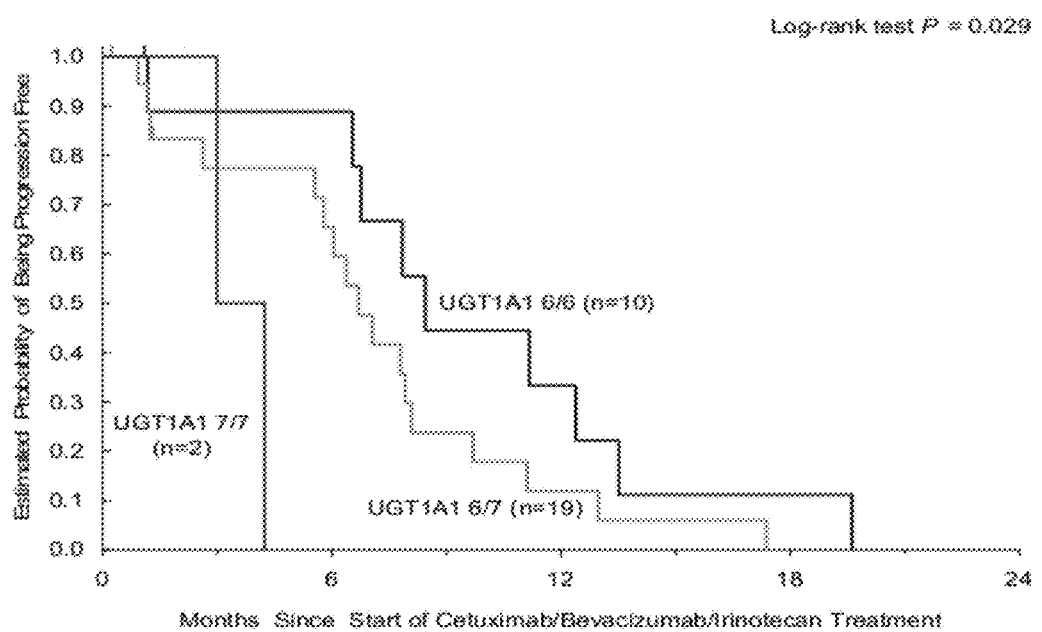
FIG. 2 shows the predictive response to CBI therapy associated with UGT1A1 (UGT1A1*28) polymorphism and progression free survival. Patients identified as having the genotype 6/6 or 6/7 show an increase in progression free survival. The letter n equals the number of patients in each group.
Figure 3:
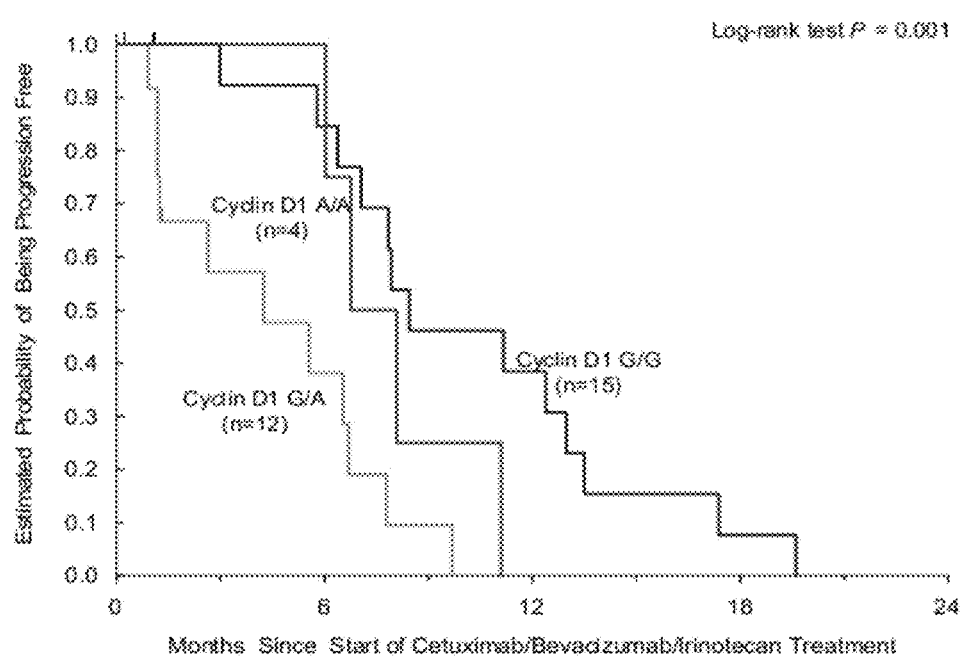
FIG. 3 shows the predictive response to CBI therapy associated with Cyclin D1 (A870G) polymorphism and progression free survival. Patients identified as having the genotype A/A or G/G show an increase in progression free survival. The letter n equals the number of patients in each group.
Figure 4:
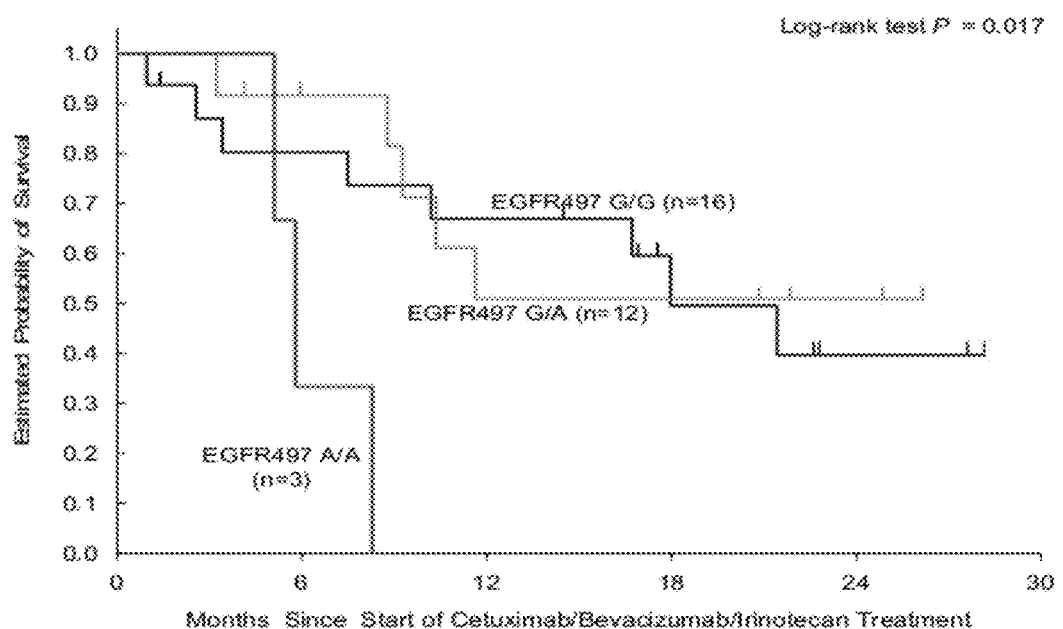
FIG. 4 shows the predictive response to CBI therapy associated with EGFR (G497A) polymorphism and overall survival. Patients identified as having the genotype G/G or G/A show an increase in progression free survival. The letter n equals the number of patients in each group.
Figure 5:
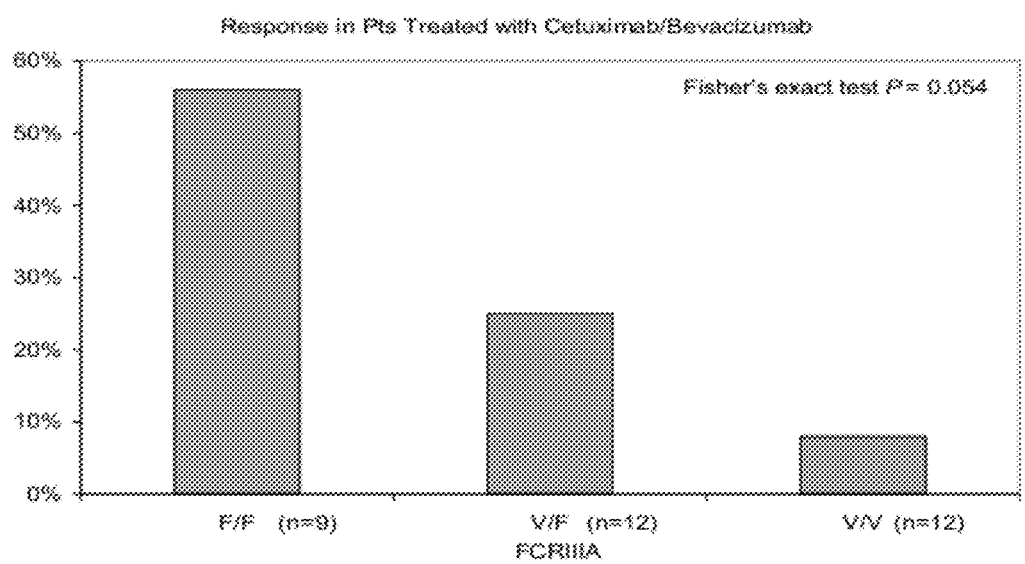
FIG. 5 shows the predictive response to CB therapy associated with FCGRIIIA (V158F) polymorphism and tumor response. Patients identified as having the genotype F/F or V/V show an increase in response. The letter n equals the number of patients in each group.
Figure 6:
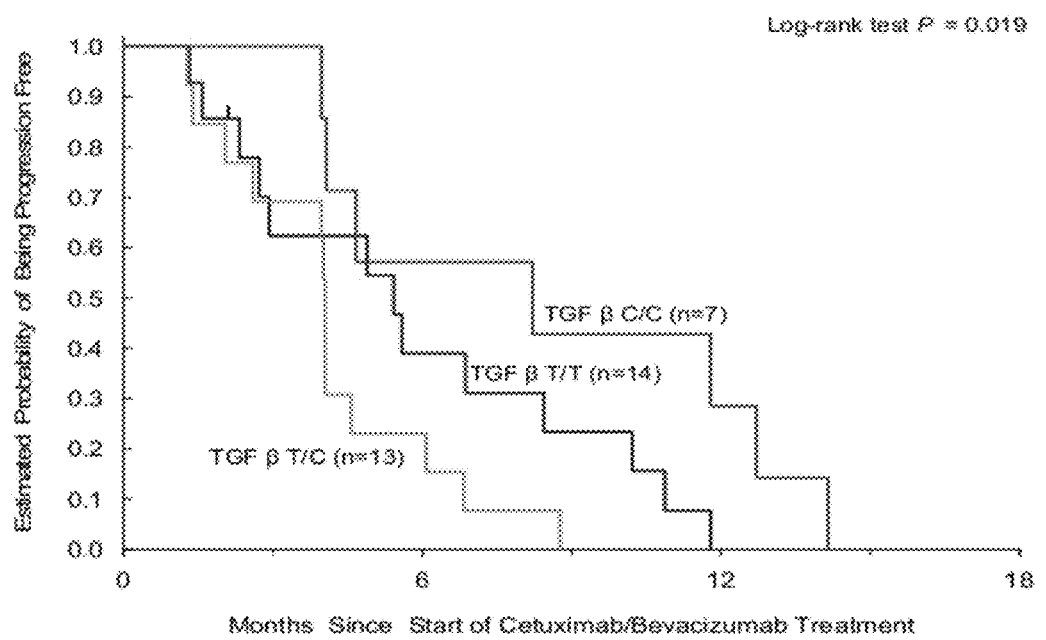
FIG. 6 shows the predictive response to CB therapy associated with TGF-β (T29C) polymorphism and progression free survival. Patients identified as having the genotype C/C or T/T show an increase in progression free survival. The letter n equals the number of patients in each group.
Figure 7:
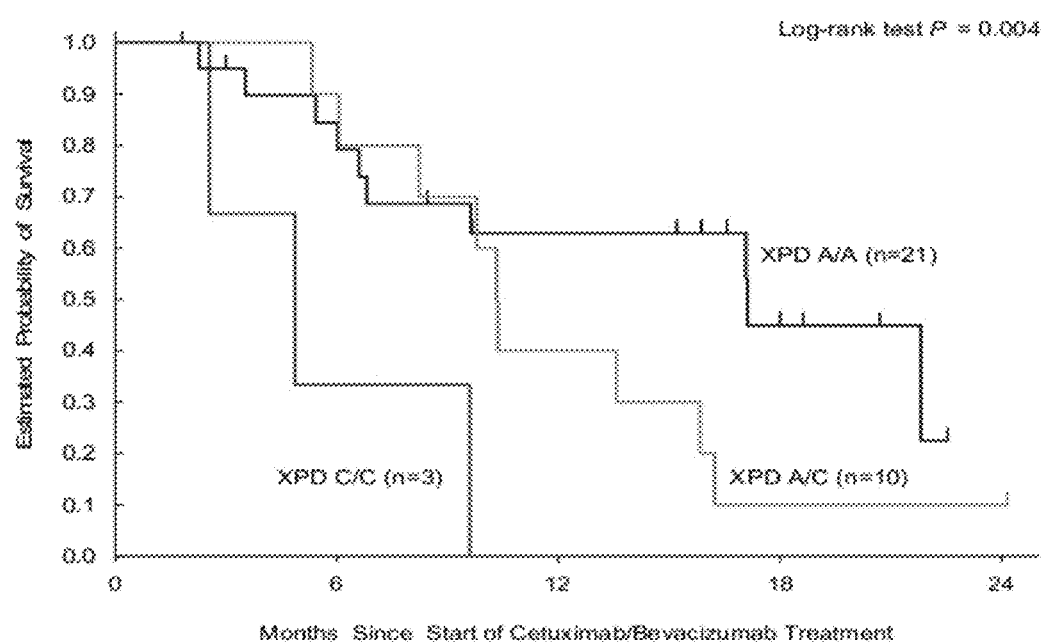
FIG. 7 shows the predictive response to CB therapy associated with XPD (A751C) polymorphism and overall survival. Patients identified as having the genotype A/A or A/C show an increase in progression free survival. The letter n equals the number of patients in each group.

Results For Arm A, significant associations were found between TGF-β polymorphism and tumor response (FIG. 1), between UGT1A1, Cyclin D1 A870G and TTP (FIGS. 2 and 3), and between EGFR497 and OS (FIG. 4) (P values <0.05). For Arm B, a trend in association was found between FCGR3A and tumor response (FIG. 5, P=0.054), and significant associations were found between XPD, TGF-β and TTP (FIG. 6), and between XPD and OS (FIG. 7) (P values <0.05).

Example 2

Background In an expansion of Experimental Example 1, a phase II CBI VS CB trial has shown that bevacizumab added the efficacy of cetuximab and cetuximab/irinotecan in irinotecan-refractory bevacizumab-naïve CRC patients. Germline polymorphisms involved in angiogenesis (VEGF, IL-8, TGF-β), EGFR pathway (EGFR, COX-2, CyclinD1, E-cadherin, FCGRIIA, FCGRIIIA), DNA repair (ERCC1, XRCC1, XPD) and drug metabolism pathway (GSTP1, UGT1A1) were tested to evaluate their association with clinical outcome. Here, gene polymorphisms data was expanded to involve EGFR pathway (EGF, FCGR2B, Survivin, ADAMS10/17), Angiogenesis pathway (Neuropilin-1, HIF-1, Tissue factor) and irinotecan metabolism pathway (ABCB1, OATPC).

Methods Genomic DNA was extracted from blood samples. 65 out of 81 patients enrolled in the BOND 2 trial were available for molecular correlates study. these 65 patients include 44 men, 21 women, median age 58 years (range 24-86). Patients received either with CBI (n=31) (Arm A) or with CB (n=34) (Arm B). In Arm A, 12 pts (43%) had PR, the median TTP was 7.1 months, and the median survival was 18.0 months. In Arm B, 9 pts (27%) had PR, the median TTP was 4.6 months, and the median survival was 10.3 months. PCR-RFLP based technique was used to determine polymorphisms. Univariate analysis (Fisher's exact test for response; log-rank test for TTP and OS) was performed to examine associations between polymorphisms and clinical outcome. Probes and primers for this analysis are known in the art as described herein, examples of which are provided in Table 5.

Results For Arm B, significant associations were found between HIF-1 and FCGRIIIA polymorphisms and tumor response (Table 7, P=0.017), between HIF-1, FCGRIIB, TGF-β, XPD, and OATPC polymorphisms and TTP (Table 8), and between OATPC, XPD, and FCGRIIIA polymorphisms and OS (Table 9, P values <0.05). For Arm A, significant association were found between TGF-β polymorphism and tumor response (Table 7, P=0.045), a significant association between UGT1A1 and Cyclin D1 polymorphisms and time to tumor progression (Table 8, P values <0.05), a trend towards association of ERCC1 and EGFR polymorphisms and time to tumor progression (Table 8), and significant association between GSTP1 and EGFR polymorphisms and overall survival (Table 9).

TABLE 7

Significant association with germline variations and response to treatment

| Polymorphism | Cetuximab/Bevacizumab/Irinotecan | | | | Cetuximab/Bevacizumab | | | |
|---|---|---|---|---|---|---|---|---|
| | N | Response | No-response | P | N | Response | No-response | P |
| TGF-β-29 | | | | 0.045 | | | | 0.17 |
| T/T | 6 | 3(50%) | 3(50%) | | 13 | 3(23%) | 10(77%) | |
| T/C | 14 | 3(21%) | 11(79%) | | 13 | 2(15%) | 11(85%) | |
| C/C | 8 | 6(75%) | 2(25%) | | 7 | 4(57%) | 3(43%) | |
| FCGRIIIA 158 | | | | 1.00 | | | | 0.054 |
| F/F | 10 | 4(40%) | 6(60%) | | 9 | 5(56%) | 4(44%) | |
| V/F | 8 | 4(50%) | 4(50%) | | 12 | 3(25%) | 9(75%) | |
| V/V | 10 | 4(40%) | 6(60%) | | 12 | 1(8%) | 11(92%) | |
| HIF1-α-1772 | | | | 0.70 | | | | 0.015 |
| C/C | 17 | 8(47%) | 9(53%) | | 30 | 6(20%) | 24(80%) | |
| C/T or T/T | 11 | 4(36%) | 7(64%) | | 3 | 3(100%) | 0(0%) | |

TABLE 8

Significant association with germline polymorphisms and time to tumor progression (TTP)

| | Cetuximab/Bevacizumab/Irinotecan | | | Cetuximab/Bevacizumab | | |
|---|---|---|---|---|---|---|
| | N | Median, Mo (95% CI) | Relative Risk (95% CI) | P | N | Median, Mo (95% CI) | Relative Risk (95% CI) | P |
| TGF-β-29 | | | | 0.11 | | | | 0.019 |
| T/T | 6 | 3.0 (1.2, 6.5) | 1.00 (Reference) | | 14 | 5.4 (2.7, 8.4) | 1.00 (Reference) | |
| T/C | 16 | 7.9 (6.4, 8.4) | 0.57 (0.21, 1.56) | | 13 | 4.0 (2.6, 4.6) | 1.69 (0.74, 3.86) | |
| C/C | 9 | 6.8 (5.8, 17.4) | 0.36 (0.11, 1.14) | | 7 | 8.2 (4.1, 12.7) | 0.55 (0.20, 1.46) | |
| UGT1A1*28 | | | | 0.029 | | | | 0.21 |
| 6/6 | 10 | 8.4 (6.8, 12.4) | 1.00 (Reference) | | 20 | 4.0 (2.9, 6.8) | 1.00 (Reference) | |
| 6/7 or 8 | 19 | 6.7 (5.8, 8.1) | 1.76 (0.76, 4.06) | | 11 | 5.6 (4.0, 8.8) | 0.65 (0.30, 1.41) | |
| 7/7 | 2 | 3.0 (3.0, 4.2) | 5.87 (0.90, 38.07) | | 3 | 6.1 (2.3, 14.2) | 0.45 (0.11, 1.75) | |
| ERCC1-118 | | | | 0.071 | | | | 0.94 |
| C/C | 7 | 8.1 (6.0, 13.5) | 1.00 (Reference) | | 14 | 4.9 (2.9, 8.2) | 1.00 (Reference) | |
| C/T | 10 | 5.8 (3.0, 6.7) | 2.47 (0.80, 7.63) | | 8 | 4.1 (2.3, 6.9) | 1.16 (0.46, 2.94) | |
| T/T | 14 | 7.8 (5.6, 11.2) | 1.10 (0.39, 3.12) | | 12 | 4.0 (4.0, 8.8) | 1.04 (0.47, 2.30) | |
| XPD 751 | | | | 0.26 | | | | 0.021 |
| A/A | 12 | 7.8 (2.6, 12.4) | 1.00 (Reference) | | 21 | 6.1 (4.0, 8.8) | 1.00 (Reference) | |
| A/C | 17 | 7.1 (6.4, 8.1) | 1.08 (0.48, 2.40) | | 10 | 4.1 (4.0, 5.6) | 1.46 (0.65, 3.30) | |
| C/C | 2 | 4.2 (4.2, 6.0) | 3.14 (0.58, 16.97) | | 3 | 2.3 (1.3, 4.0) | 4.49 (1.13, 17.93) | |
| EGFR 497 | | | | 0.065 | | | | 0.83 |
| G/G | 16 | 8.1 (6.0, 11.2) | 1.00 (Reference) | | 19 | 4.6 (4.0, 5.6) | 1.00 (Reference) | |
| G/A | 12 | 6.7 (5.8, 7.8) | 1.48 (0.66, 3.32) | | 12 | 4.0 (2.6, 6.9) | 0.98 (0.47, 2.07) | |
| A/A | 3 | 2.6 (2.6., 5.6) | 4.60 (0.78, 27.03) | | 3 | 8.2 (2.7, 11.8) | 0.70 (0.20, 2.40) | |
| CyclinD1 870 | | | | 0.001 | | | | 0.21 |
| G/G | 15 | 8.4 (7.1, 13.0) | 1.00 (Reference) | | 13 | 4.0 (2.9, 5.4) | 1.00 (Reference) | |
| G/A | 12 | 4.2 (1.2, 6.7) | 3.64 (1.37, 9.65) | | 13 | 6.9 (4.0, 8.4) | 0.52 (0.23, 1.19) | |
| A/A | 4 | 6.8 (6.0, 11.1) | 1.67 (0.49, 5.60) | | 8 | 4.0 (2.6, 10.2) | 0.73 (0.30, 1.79) | |
| HIF1-α 1772 | | | | 0.40 | | | | 0.019 |
| C/C | 20 | 6.8 (5.6, 9.7) | 1.00 (Reference) | | 31 | 4.1 (4.0, 5.6) | 1.00 (Reference) | |
| C/T or T/T | 11 | 7.1 (4.2, 11.1) | 1.37 (0.61, 3.07) | | 3 | 11.8 (8.8, 14.2) | 0.31 (0.09, 1.08) | |
| OATPC 388 | | | | 0.55 | | | | 0.064 |
| A/A | 9 | 6.4 (1.2, 12.4) | 1.00 (Reference) | | 13 | 6.9 (4.9, 10.9) | 1.00 (Reference) | |
| A/G | 17 | 6.8 (6.0, 7.9) | 1.33 (0.52, 3.38) | | 12 | 4.0 (2.7, 5.4) | 1.71 (0.74, 3.91) | |
| G/G | 4 | 1.2 (1.2, 17.4) | 0.81 (0.24, 2.76) | | 7 | 4.0 (2.3, 4.1) | 2.66 (0.98, 7.19) | |

TABLE 8-continued

Significant association with germline polymorphisms and time to tumor progression (TTP)

| | Cetuximab/Bevacizumab/Irinotecan | | | | Cetuximab/Bevacizumab | | |
|---|---|---|---|---|---|---|---|
| | N | Median, Mo (95% CI) | Relative Risk (95% CI) | P | N | Median, Mo (95% CI) | Relative Risk (95% CI) | P |
| FCGRIIB 232 | | | | 0.29 | | | | 0.054 |
| T/T | 22 | 6.8 (4.2, 9.7) | 1.00 (Reference) | | 21 | 4.7 (4.0, 6.9) | 1.00 (Reference) | |
| T/C | 8 | 7.8 (6.0, 17.4) | 0.58 (0.22, 1.50) | | 9 | 4.6 (4.0, 11.8) | 0.82 (0.36, 1.87) | |
| C/C | 1 | 6.4 | 1.79 (0.21, 14.93) | | 2 | 1.3 | 4.38 (0.88, 21.90) | |

TABLE 9

Significant association with germline polymorphisms and overall survival (OS)

| | Cetuximab/Bevacizumab/Irinotecan | | | | Cetuximab/Bevacizumab | | | |
|---|---|---|---|---|---|---|---|---|
| | N | Median, MO (95% CI) | Relative Risk (95% CI) | P | N | Median, MO (95% CI) | Relative Risk (95% CI) | P |
| XPD 751 | | | | 0.87 | | | | 0.004 |
| A/A | 12 | 21.4 (5.1, 28.2) | 1.00 (Reference) | | 21 | 17.1 (6.8, 22.5) | 1.00 (Reference) | |
| A/C | 17 | 10.3 (8.3, 27.6) | 1.28 (0.45, 3.63) | | 10 | 10.3 (8.2, 15.8) | 1.88 (0.76, 4.68) | |
| C/C | 2 | 10.2 (10.2, 20.8+) | 0.91 (0.11, 7.69) | | 3 | 4.9 (2.5, 9.6) | 6.64 (1.55, 28.54) | |
| GSTP1 105 | | | | 0.052 | | | | 0.61 |
| I/I | 10 | 11.6 (5.8, 21.4) | 1.00 (Reference) | | 14 | 13.6 (4.9, 21.8) | 1.00 (Reference) | |
| V/I | 16 | 28.2+ (10.3, 28.2+) | 0.34 (0.11, 1.09) | | 14 | 15.8 (9.6, 22.5) | 0.73 (0.28, 1.91) | |
| V/V | 5 | 7.5 (2.6, 24.8) | 1.40 (0.40, 4.85) | | 6 | 9.8 (8.2, 17.1) | 1.25 (0.40, 3.86) | |
| FCGRIIIA 158 | | | | 0.93 | | | | 0.057 |
| F/F | 11 | 21.4 (9.3, 28.2) | 1.00 (Reference) | | 10 | 8.2 (6.0, 24.1) | 1.00 (Reference) | |
| V/F | 9 | 18.0 (8.3, 24.8) | 1.18 (0.34, 4.09) | | 12 | 17.1 (13.6, 22.5) | 0.50 (0.16, 1.56) | |
| V/V | 11 | 16.7 (7.5, 26.2) | 1.26 (0.38, 4.17) | | 12 | 9.6 (4.9, 10.3) | 1.69 (0.63, 4.52) | |
| EGFR 497 | | | | 0.017 | | | | 0.41 |
| G/G | 16 | 18.0 (10.2, 28.2) | 1.00 (Reference) | | 19 | 9.6 (6.8, 17.1) | 1.00 (Reference) | |
| G/A | 12 | 26.2+ (9.3, 26.2+) | 0.85 (0.28, 2.57) | | 12 | 15.8 (4.9, 21.8) | 0.76 (0.30, 1.92) | |
| A/A | 3 | 5.8 (5.1, 8.3) | 4.62 (0.96, 22.29) | | 3 | 3 | 0.30 (0.04, 2.25) | |
| OATPC 388 | | | | 0.72 | | | | 0.002 |
| A/A | 9 | 27.6+ (3.2, 27.6+) | 1.00 (Reference) | | 13 | 24.1+ (17.1, 24.1+) | 1.00 (0.00, 0.00) | |
| A/G | 17 | 16.7 (9.3, 21.4) | 1.14 (0.36, 3.60) | | 12 | 8.2 (6.0, 13.6) | 5.51 (1.58, 19.27) | |
| G/G | 4 | 28.2+ (3.4, 28.2+) | 0.51 (0.06, 4.49) | | 7 | 6.0 (4.9, 10.3) | 7.56 (1.83, 31.16) | |

Example 3

Background In an expansion of Experimental Examples 1 and 2, the phase II (BOND2) trial of Cetuximab/Bevacizumab/Irinotecan (CBI) vs Cetuximab/Bevacizumab (CB) has shown that bevacizumab added to the efficacy of cetuximab and cetuximab/irinotecan in irinotecan-refractory bevacizumab-naïve CRC patients. Expression levels of genes involved in angiogenesis (VEGF, IL-8), the EGFR pathway (EGFR, COX2) and DNA repair (ERCC1) were evaluated to identify if they were associated with clinical outcome.

Methods This randomized phase II trial enrolled 81 patients. Treatment plan as: Arm A received IRI at the same dose and schedule as last received prior to study, plus Cetuximab 400 mg/m2 loading dose, then weekly at 250 mg/m2, plus Bevacizumab 5 mg/kg given every other week. Arm B received the same as arm A, but without IRI. FFPE samples for 35 out of 81 patients (M:W 24:11, median age 56 (29-80) enrolled in the BOND2 study were tested. Patients received either with CBI (n=18, Arm A) or with CB (n=17, Arm B). FFPE tissues were dissected using laser-captured microdissection and analyzed EGFR, ERCC1, VEGFA, VEGFR2, COX2, Cyclin D1, IL-8, and NRP1 mRNA expression using a quantitative real-time RT-PCR. Gene expression values are expressed as ratios between the target gene and internal reference gene (β-actin). Probes and primers for this analysis are known in the art as described herein, examples of which are provided in Table 5.

Figure 8:
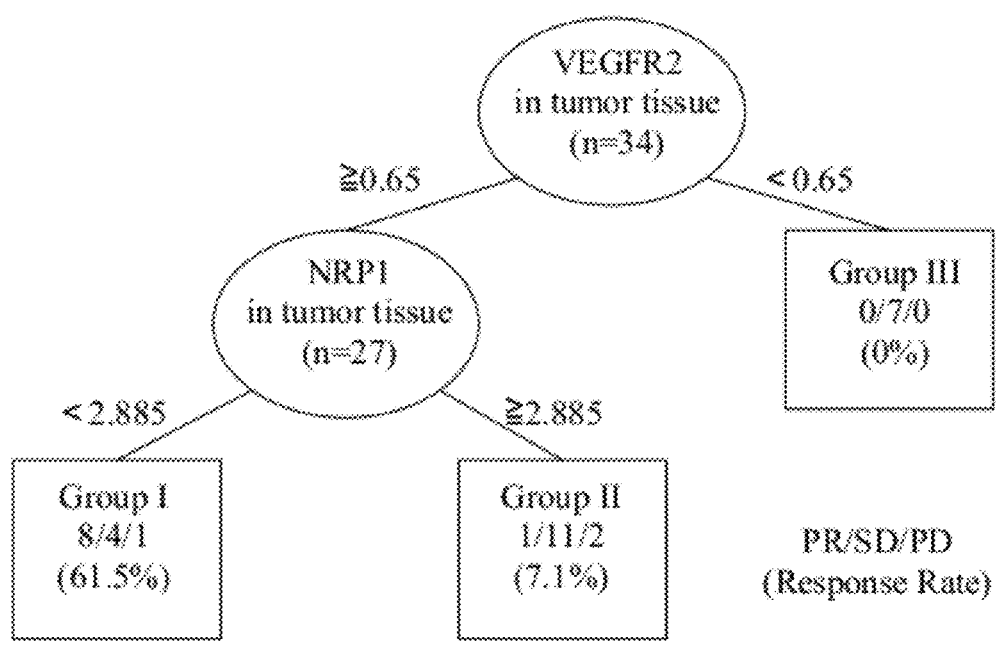
FIG. 8 shows a tree diagram for predictive response to CBI therapy associated with intratumoral gene expression of VEGFR2 and NRP1 using CART analysis. Patients identified as having the genetic markers of Group I show a 61.5% response rate.
Figure 9:
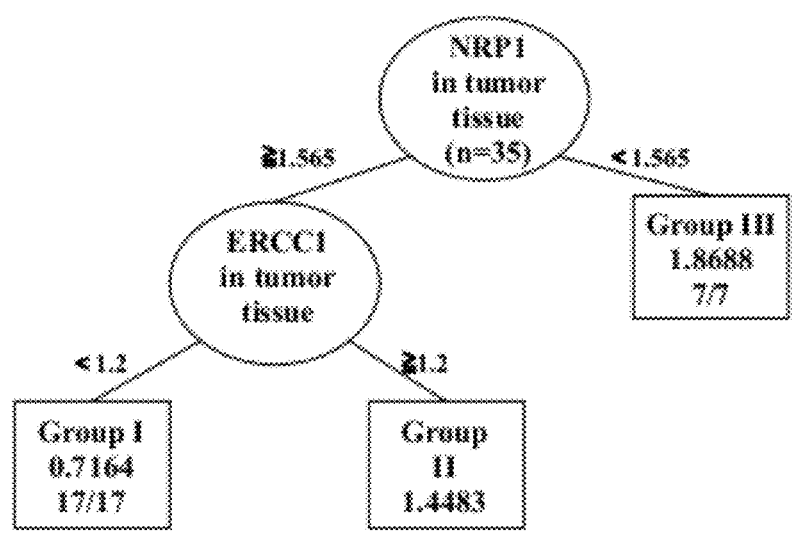
FIG. 9 shows a tree diagram for predictive response to CBI therapy associated with intratumoral gene expression of NRP1 and ERCC1 using CART analysis. Patients identified as having the genetic markers of Group I show lower risk for progression.
Figure 10:
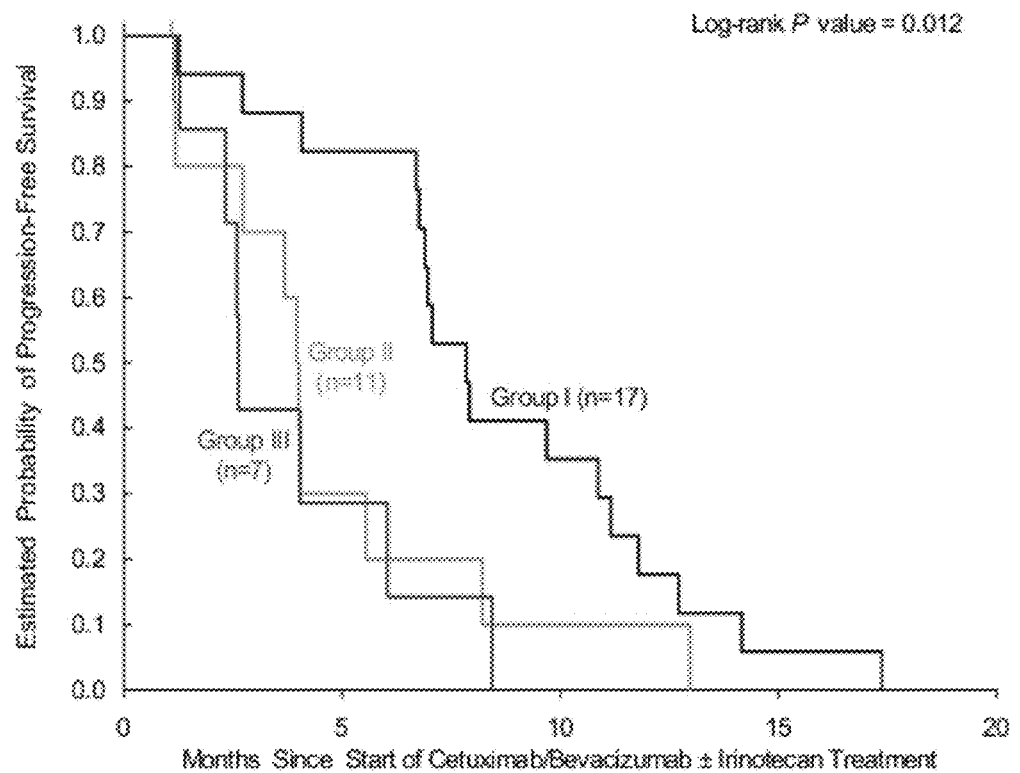
FIG. 10 shows a predictive survival curve for patient receiving CBI therapy categorized into Groups I, II, and III as identified in FIG. 9. Patients identified as having the genetic markers of Group I show an increase in progression free survival. The letter n equals the number of patients in each group.
Figure 11:
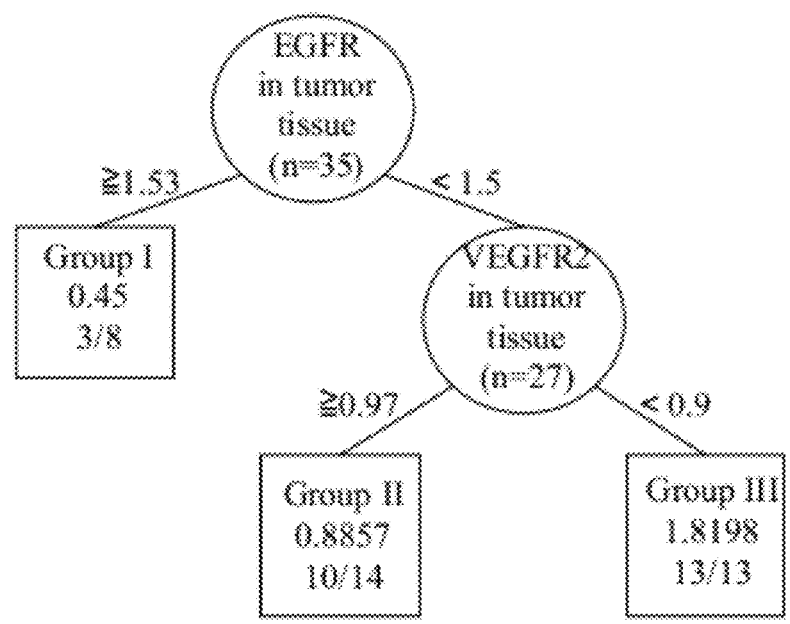
FIG. 11 shows a tree diagram for predictive response to CBI therapy associated with intratumoral gene expression of EGFR and VEGFR2 using CART analysis. Patients identified as having the genetic markers of Group I or II show lower risk for progression.
Figure 12:
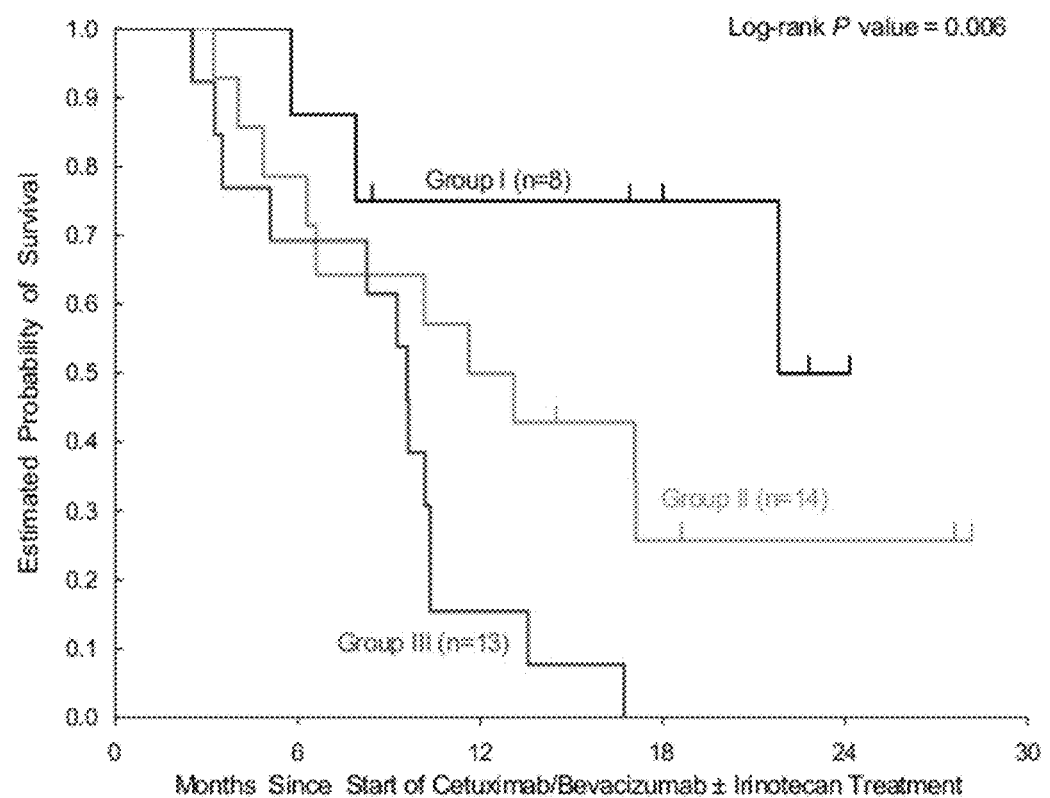
FIG. 12 shows a predictive survival curve for patient receiving CBI therapy categorized into Groups I, II, and III as identified in FIG. 11. Patients identified as having the genetic markers of Groups I and II show an increase in progression free survival. The letter n equals the number of patients in each group.

Results All eight genes and treatment Arm were considered in the CART analysis. The classification tree for response, progression-free survival, and overall survival are evaluated. The expression levels of VEGFR2 and NRP1 classified patients in 3 response groups with response rate range from 61% to 0%. Patients who were classified as responders (Group I; VEGFR2 ≧0.65 and NRP1 <2.285) were at a lower risk for progression (FIG. 8), compared with patients who were classified as non-responders (Group II; VEGFR2 ≧0.65 and NRP1 ≧2.285 and Group III; VEGFR2 <0.65). The expression levels of NRP1 and ERCC1, and EGFR and VEGFR2 were chosen to classify patients into 3 groups with distinct risk of progression-free survival and overall survival, respectively. Patient who were classified as being at a lower risk for progression (Group I; NRP ≧1.565 and ERCC1 <1.2), compared to patients who were classified as groups II or III (FIGS. 9 and 10). Patient who were classified as being at a lower risk for overall survival (Group I; EGFR $\geq$1.535 or Group II; EGFR <1.535 and VEGFR2 $\geq$0.975), compared to patients who were classified as group III (FIGS. 11 and 12).

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for determining if a colorectal cancer patient is likely or is not likely responsive to therapy comprising the administration of an effective amount of Cetuximab and Bevacizumab and said therapy does not include irinotecan, comprising screening a suitable cell or tissue sample isolated from said patient for the genetic marker of FCGRIIIA (V158F), and the presence of (F/F or V/F) for FCGRIIIA (V158F) in the sample, indicates the patient will likely be responsive to the therapy and the absence of the marker indicates that the patient will not likely be responsive to the therapy.

2. The method of claim 1, wherein the colorectal cancer patient is suffering from metastatic colorectal cancer.

3. The method of claim 1, wherein the suitable cell or tissue sample is a tumor cell or tissue sample.

4. The method of claim 1, wherein the suitable cell or tissue sample is a metastatic colorectal tumor cell or tissue sample.

5. The method of claim 1, wherein the suitable cell or tissue sample is a normal cell or tissue sample.

6. The method of claim 1, wherein the suitable cell or tissue sample is peripheral blood lymphocytes.

7. A method for treating a human colorectal cancer patient comprising administering a therapy comprising an effective amount of Cetuximab and Bevacizumab and said therapy does not include irinotecan, to the human colorectal cancer patient selected for said therapy based on having the genetic marker of (F/F or V/F) for FCGRIIIA (V158F) in a sample isolated from the patient thereby treating said patient.

8. A method for determining if a human colorectal cancer patient is likely or is not likely responsive to therapy consisting of the administration of an effective amount of Cetuximab and Bevacizumab, said method comprising screening a suitable cell or tissue sample isolated from said patient for the genetic marker FCGRIIIA (V158F) and, and the presence of the genetic marker, (F/F or V/F) for FCGRIIIA (V158F), indicates the patient will likely be responsive to the therapy and wherein the absence of the marker indicates that the patient is not likely responsive to the therapy.

9. The method of claim 8, wherein the colorectal cancer patient is suffering from metastatic colorectal cancer.

10. The method of claim 8, wherein the response comprises an improvement in a clinical endpoint selected from the group consisting of time to tumor progression and overall survival.

11. A method for treating a human colorectal cancer patient consisting of administering an effective amount of Cetuximab and Bevacizumab, to a the human colorectal cancer patient selected for said therapy based on having the genetic marker of (F/F or V/F) for FCGRIIIA (V158F) in a patient sample, thereby treating said patient.

12. The method of claim 11, wherein the colorectal cancer patient is suffering from metastatic colorectal cancer.

13. The method of claim 11, wherein treating comprises an improvement in a clinical endpoint selected from the group consisting of time to tumor progression and overall survival.

14. The method of claim 1, wherein responsive to therapy correlates with a positive tumor response to the therapy.

* * * * *